(12) United States Patent
Ward et al.

(10) Patent No.: US 12,090,261 B2
(45) Date of Patent: Sep. 17, 2024

(54) METHOD FOR MODULATING ENDOTHELIAL GLYCOCALYX STRUCTURE

(71) Applicant: ExThera Medical Corporation, Martinez, CA (US)

(72) Inventors: Robert S. Ward, Martinez, CA (US); Keith R. McCrea, Martinez, CA (US); Lakhmir (Mink) Chawla, Martinez, CA (US)

(73) Assignee: EXTHERA MEDICAL CORPORATION, Martinez, CA (US)

( * ) Notice: Subject to any disclaimer, the term of this patent is extended or adjusted under 35 U.S.C. 154(b) by 338 days.

(21) Appl. No.: 17/526,663

(22) Filed: Nov. 15, 2021

(65) Prior Publication Data

US 2022/0072038 A1 Mar. 10, 2022

Related U.S. Application Data

(63) Continuation of application No. PCT/US2020/032150, filed on May 8, 2020.
(Continued)

(51) Int. Cl.
*A61K 31/727* (2006.01)
*A61K 31/726* (2006.01)
(Continued)

(52) U.S. Cl.
CPC ......... *A61M 1/3689* (2014.02); *A61K 31/726* (2013.01); *A61K 31/727* (2013.01);
(Continued)

(58) Field of Classification Search
CPC .................................................. A61K 31/727
See application file for complete search history.

(56) References Cited

U.S. PATENT DOCUMENTS

| | | |
|---|---|---|
| 3,782,382 A | 1/1974 | Naftulin et al. |
| 4,048,064 A | 9/1977 | Clark, III |
| | (Continued) | |

FOREIGN PATENT DOCUMENTS

| | | |
|---|---|---|
| CN | 1395620 A | 2/2003 |
| CN | 101370536 A | 2/2009 |
| | (Continued) | |

OTHER PUBLICATIONS

Uchimido et al., "The glycocalyx: a novel diagnostic and therapeutic target in sepsis," Critical Care 23(16):1-12, 2019.*
(Continued)

*Primary Examiner* — Rosanne Kosson
(74) *Attorney, Agent, or Firm* — Kilpatrick Townsend & Stockton LLP

(57) ABSTRACT

The present invention provides methods and devices for augmenting impaired glycocalyx barrier function in a subject in need thereof by contacting a sample (e.g., blood) obtained from the subject with a glycocalyx-mimetic adsorption media. The adsorption media includes glycosaminoglycan structures and, optionally, proteoglycan core proteins, which are conducive to enhancing and/or restoring the impaired glycocalyx barrier function in a sample. The contacted sample is subsequently separated from the adsorption media, producing a treated sample that can be infused into the subject. Methods and devices for treating a patient suffering from a disease associated with glycocalyx barrier dysfunction are also provided herein.

17 Claims, 3 Drawing Sheets

Related U.S. Application Data

(60) Provisional application No. 62/848,819, filed on May 16, 2019.

(51) Int. Cl.
        A61K 31/728      (2006.01)
        A61K 31/737      (2006.01)
        A61M 1/36        (2006.01)
        A61P 7/00        (2006.01)
        B01J 20/24       (2006.01)

(52) U.S. Cl.
     CPC .......... *A61K 31/728* (2013.01); *A61K 31/737* (2013.01); *A61P 7/00* (2018.01); *B01J 20/24* (2013.01)

(56) References Cited

U.S. PATENT DOCUMENTS

| | | |
|---|---|---|
| 4,103,685 A | 8/1978 | Lupien et al. |
| 4,358,376 A | 11/1982 | Moriuchi et al. |
| 4,415,665 A | 11/1983 | Mosbach et al. |
| 4,430,496 A | 2/1984 | Abbott |
| 4,599,165 A | 7/1986 | Chevallet |
| 4,613,665 A | 9/1986 | Larm |
| 4,637,994 A | 1/1987 | Tani et al. |
| 4,643,896 A | 2/1987 | Asakura et al. |
| 4,820,302 A | 4/1989 | Woodroof |
| 4,955,870 A | 9/1990 | Ridderheim et al. |
| 5,116,962 A | 5/1992 | Stueber et al. |
| 5,211,850 A | 5/1993 | Shettigar et al. |
| 5,227,049 A | 7/1993 | Chevallet et al. |
| 5,318,511 A | 6/1994 | Riquier et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,679,775 A | 10/1997 | Boos et al. |
| 5,753,227 A | 5/1998 | Strahilevitz |
| 5,773,384 A | 6/1998 | Davankov et al. |
| 5,858,238 A | 1/1999 | McRea |
| 6,037,458 A | 3/2000 | Hirai et al. |
| 6,159,377 A | 12/2000 | Davankov et al. |
| 6,197,568 B1 | 3/2001 | Marks et al. |
| 6,238,795 B1 | 5/2001 | Strom |
| 6,248,127 B1 | 6/2001 | Shah et al. |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 | 4/2010 | Soundarrajan et al. |
| 8,273,357 B2 | 9/2012 | Hacohen et al. |
| 8,663,148 B2 | 3/2014 | Larm et al. |
| 8,758,286 B2 | 6/2014 | Ward et al. |
| 9,173,989 B2 | 11/2015 | Larm et al. |
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 10,457,974 B2 | 10/2019 | Ward et al. |
| 10,487,350 B2 | 11/2019 | Ward et al. |
| 10,537,280 B2 | 1/2020 | McCrea et al. |
| 10,639,413 B2 | 5/2020 | McCrea et al. |
| 10,688,239 B2 | 6/2020 | Larm et al. |
| 10,786,615 B2 | 9/2020 | Ward et al. |
| 10,857,283 B2 | 12/2020 | Ward et al. |
| 11,065,378 B2 | 7/2021 | Larm et al. |
| 11,123,466 B2 | 9/2021 | Ward et al. |
| 11,266,772 B2 | 3/2022 | McCrea et al. |
| 11,306,346 B2 | 4/2022 | Ward et al. |
| 2001/0005487 A1 | 6/2001 | Kamibayashi et al. |
| 2002/0018985 A1 | 2/2002 | Eible et al. |
| 2002/0040012 A1 | 4/2002 | Stiekema et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2003/0231981 A1 | 12/2003 | Johnson |
| 2004/0054320 A1 | 3/2004 | Kissinger et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182763 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0205476 A1 | 9/2005 | Chevallet et al. |
| 2005/0244371 A1 | 11/2005 | Lentz |
| 2005/0271653 A1 | 12/2005 | Strahilevitz |
| 2006/0030027 A1 | 2/2006 | Ellson et al. |
| 2006/0076295 A1 | 4/2006 | Leonard et al. |
| 2006/0093999 A1 | 5/2006 | Hei |
| 2006/0134595 A1 | 6/2006 | Rapp et al. |
| 2006/0252054 A1 | 11/2006 | Lin et al. |
| 2007/0190050 A1 | 8/2007 | Davidner et al. |
| 2007/0218514 A1 | 9/2007 | Smith et al. |
| 2007/0231217 A1 | 10/2007 | Clinton et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0186065 A1 | 7/2009 | Tillman et al. |
| 2009/0206038 A1 | 8/2009 | Thomas |
| 2009/0246800 A1 | 10/2009 | Mattingly et al. |
| 2009/0325276 A1 | 12/2009 | Battrell et al. |
| 2010/0021622 A1 | 1/2010 | Meng et al. |
| 2010/0040546 A1 | 2/2010 | Hyde et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt et al. |
| 2010/0249689 A1 | 9/2010 | Larm et al. |
| 2010/0276359 A1 | 11/2010 | Ippommatsu et al. |
| 2010/0291588 A1 | 11/2010 | McDevitt et al. |
| 2010/0326916 A1 | 12/2010 | Wrazel et al. |
| 2011/0137224 A1 | 6/2011 | Ibragimov |
| 2011/0150911 A1 | 6/2011 | Choo et al. |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0097613 A1 | 4/2012 | Hoshino et al. |
| 2012/0219561 A1 | 8/2012 | Alt et al. |
| 2012/0244557 A1 | 9/2012 | Yu et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0074007 A1 | 3/2014 | McNeil |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2015/0374898 A1 | 12/2015 | Fujieda et al. |
| 2016/0003858 A1 | 1/2016 | McKendry et al. |
| 2016/0022898 A1 | 1/2016 | Larm et al. |
| 2016/0082177 A1 | 3/2016 | Ward et al. |
| 2016/0084835 A1 | 3/2016 | Ward et al. |

(56) References Cited

U.S. PATENT DOCUMENTS

| | | | |
|---|---|---|---|
| 2016/0101229 A1 | 4/2016 | McCrea et al. |
| 2016/0214935 A1 | 7/2016 | Hutchinson et al. |
| 2016/0243525 A1 | 8/2016 | Song et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0252502 A1 | 9/2017 | Ward et al. |
| 2017/0340803 A1 | 11/2017 | Larm et al. |
| 2018/0117237 A1 | 5/2018 | Brugger et al. |
| 2018/0361050 A1 | 12/2018 | Ward et al. |
| 2019/0038826 A1 | 2/2019 | McCrea et al. |
| 2019/0143027 A1 | 5/2019 | Larm et al. |
| 2020/0023001 A1 | 1/2020 | Ebong et al. |
| 2020/0056221 A1 | 2/2020 | Ward et al. |
| 2020/0171233 A1 | 6/2020 | McCrea et al. |
| 2020/0297913 A1 | 9/2020 | Larm et al. |
| 2020/0338256 A1 | 10/2020 | Ward et al. |
| 2021/0008269 A1 | 1/2021 | Ward et al. |
| 2024/0066470 A1 | 2/2024 | Ward et al. |

FOREIGN PATENT DOCUMENTS

| | | | |
|---|---|---|---|
| CN | 101632686 A | 1/2010 |
| CN | 101784294 A | 7/2010 |
| CN | 102740859 A | 10/2012 |
| CN | 102791307 | 11/2012 |
| CN | 106714669 A | 5/2014 |
| CN | 106178161 A | 12/2016 |
| CN | 106255520 A | 12/2016 |
| CN | 206345699 U | 7/2017 |
| CN | 107771080 A | 3/2018 |
| DE | 4217917 A1 | 12/1993 |
| EP | 0306617 A | 3/1989 |
| EP | 0321703 A | 6/1989 |
| EP | 0533946 A1 | 3/1993 |
| EP | 0616845 A | 9/1994 |
| EP | 0810027 A | 12/1997 |
| EP | 1044696 A2 | 10/2000 |
| EP | 1057529 A | 12/2000 |
| EP | 1110602 A | 6/2001 |
| EP | 1219639 A | 7/2002 |
| EP | 2087916 A1 | 8/2009 |
| EP | 2556849 A1 | 2/2013 |
| GB | 2172812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2011-509083 A | 3/2011 |
| JP | 2012-501708 A | 1/2012 |
| JP | 2013-512078 A | 4/2013 |
| JP | 2014-500735 A | 1/2014 |
| JP | 2014-523914 A | 9/2014 |
| JP | 2016-526416 A | 9/2016 |
| JP | 2017-528253 A | 9/2017 |
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2006/012885 A1 | 2/2006 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2009/086343 A2 | 7/2009 |
| WO | 2009/121959 A1 | 10/2009 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A2 | 12/2012 |
| WO | 2013/012924 A2 | 1/2013 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |
| WO | 2016/048901 A1 | 3/2016 |
| WO | 2016/164534 A1 | 10/2016 |
| WO | 2016/164787 A2 | 10/2016 |
| WO | 2017/001357 A1 | 1/2017 |
| WO | 2017/151797 A1 | 9/2017 |
| WO | 2018/047929 A1 | 3/2018 |
| WO | 2020/231830 A1 | 11/2020 |
| WO | 2021/119195 A1 | 6/2021 |
| WO | 2021/119197 A1 | 6/2021 |
| WO | 2022/216510 A1 | 10/2022 |

OTHER PUBLICATIONS

Abdul-Razzak, K. et al., "Fetal and newborn calf thymus as a source of chromatin proteins: Purification of HMG-1 and HMG-2," Preparative Biochemistry and Biotechnology, 17(1):51-61, 1987.

Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.

Alfaro et al., "Interleukin-8 in cancer pathogenesis, treatment and follow-up," Cancer Treat Rev., Nov. 2017, vol. 60:24-31 (abstract only).

Andrade-Gordon, P. et al., "Interaction of heparin with plasminogen activators and plasminogen: effects on the activation of plasminogen," Biochemistry, 25(14):4033-4040, 1986.

Andreasen, P.A. et al., "The plasminogen activation system in tumor growth, invasion, and metastasis," Cellular and Molecular Life Sciences, 57(1):25-40, 2000.

Ascencio, F. et al., "Affinity of the gastric pathogen Heficobacter py/ori for the N-sulphated glycosaminoglycan heparan sulphate," J. Med. Microbiol., 38:240-244, 1993.

Axelsson, J. et al., "Cytokines in blood from septic patients interact with surface-immobilized heparin," ASAIO Journal, 56:48-51, 2010.

(56) References Cited

OTHER PUBLICATIONS

Bartlett, A. and P. Park, "Proteoglycans in host-pathogen interactions: molecular mechanisms and therapeutic implications," Expert Rev. Mol. Med., 12(e5):1-33, 2015.
Bhakdi, S. and Tranum-Jensen, J., "Alpha-toxin of *Staphylococcus aureus*," Microbiological Reviews, 55(4):733-751, 1991.
Bindslev et al., "Treatment of acute respiratory failure by extracorporeal carbon dioxide elimination performed with a surface heparinized artificial lung," Anesthesiology, 67(1):117-120, 1987.
Bjorklund et al., Abstract of "Synthesis of silica-based heparin-affinity adsorbents," J. Chrom. A., 728(1-2):149-169, 1996.
Brat, D. et al., "The role of interleukin-8 and its receptors in gliomagenesis and tumoral angiogenesis," Neuro-oncology, 7(2):122-133, 2005.
Celik, T. et al., "Treatment of lyme neuroborreliosis with plasmapheresis," J. Clinical Apheresis, 31:476-478, 2016.
Chase, H., "Affinity separations utilising immobilised monoclonal antibodies—a new tool for the biochemical engineer," Chemical Engineering Science, 39(7-8):1099-1125, 1984.
Chen et al., "Microbial subversion of heparin sulfate proteoglycans," Mol. Cells, 26:415-426, 2008.
Choong, P.F. et al., "Urokinase plasminogen activator system: a multifunctional role in tumor progression and metastasis," Clinical Orthopaedics and Related Research, 415(Suppl):S46-58, 2003.
Cutler, R. et al., "Extracorporeal removal of drugs and poisons by hemodialysis and hemoperfusion," Ann. Rev. Pharmacol. Toxicol., 27:169-91, 1987.
Dixon et al., "Anthrax," New England Journal of Medicine, 341(11):815-826, 1999.
Dubreuil et al., "Effect of heparin binding on Helicobacter pylori resistance to serum," J. Med. Micro., 53:9-12, 2004.
Era, K. et al., "Development of Systems for Passive and Active CAVH," J. Japanese Society for Dialysis Therapy, 19(2):175-181, 1986.
Francy, D. et al., "Comparison of filters for concentrating microbial indicators and pathogens in lake water samples," Applied and Environmental Microbiology, 79(4):1342-52, 2012.
Frick, I. et al., "Interactions between M proteins of *Streptococcus pyogenes* and glycosaminoglycans promote bacterial adhesion to host cells," Eur. J. Biochem., 270(10):2303-11, 2003.
Fujita, M. et al., "Adsorption of inflammatory cytokines using a heparin-coated extracorporeal circuit," Artificial Organs, 26(12):1020-1025, 2002.
Garg, L. et al., "Isolation and separation of HMG proteins and histones H1 and H5 and core histones by col. chromatography on phosphocellulose," Protein Expression and Purification, 14(2):155-159, 1998.
GE Healthcare, "Size exclusion chromatography columns and resins, Selection guide," 2010, retrieved online at <<https://cdn.gelifesciences.com/dmm3bwsv3/AssetStream.aspx?mediaformatid=10061&destinationid=10016&assetid=13947>> on Jun. 27, 2019, 10 pages.
Ghannoum, M. et al., "Extracorporeal treatment for carbamazepine poisoning: Systematic review and recommendations from the EXTRIP workgroup," Clinical Toxicology, 52:993-1004, 2014.
Haase et al., "The effect of three different miniaturized blood purification devices on plasma cytokine concentration in an ex vivo model of endotoxinemia," Int. J. Artif. Organs, 31(8):722-729, 2008.
Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.
Hsu, C. et al., "Early hemoperfusion may improve survival of severely paraquat-poisoned patients," PLoS ONE, 7(10):e48397, 2012.
International Preliminary Report on Patentability, Aug. 21, 2013, PCT Application No. PCT/US2012/025316; 8 pages.
International Search Report; PCT/SE2006/001421 mailed Mar. 30, 2007.
International Search Report; PCT/US2010/058596 mailed Mar. 29, 2011.
International Search Report; PCT/US2011/024229 mailed May 30, 2011.
International Search Report; PCT/US2012/025316 mailed May 23, 2012.
International Search Report; PCT/US2013/042377 mailed Sep. 9, 2013.
International Search Report; PCT/US2014/043358 mailed Dec. 1, 2014.
International Search Report; PCT/US2014/064419 mailed Feb. 12, 2015.
International Search Report; PCT/US2015/026340 mailed Jul. 28, 2015.
International Search Report; PCT/US2015/051239 mailed Dec. 17, 2015.
International Search Report; PCT/US2016/057121 mailed Dec. 30, 2016.
International Search Report; PCT/US2017/020243 mailed May 19, 2017.
International Search Report; PCT/US2017/058536; mailed Jan. 17, 2018.
International Search Report; PCT/US2020/032150; mailed Jul. 24, 2020.
International Search Report; PCT/US2020/064112; mailed Mar. 10, 2021.
International Search Report; PCT/US2020/064110; mailed Apr. 13, 2021.
International Search Report; PCT/US2022/022748; mailed Aug. 17, 2022.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Keuren et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Kishimoto, S. et al., "Human stem cell factor (SCF) is a heparin-binding cytokine," J. Biochem., 145(3):275-278, 2009.
Kumari, N. et al., "Role of interleukin-6 in cancer progression and therapeutic resistance," Tumour Biol., Sep. 2016, vol. 37(9), pp. 11553-11572 (abstract only).
Larm et al., "A new non-thrombogenic surface prepared by selective covalent binding of heparin via a modified reducing terminal residue," Biomater Med Devices Artif Organs, 11(2&3):161-173, 1983.
Lemaire, M. et al., "Treatment of paediatric vancomycin intoxication: a case report and review of the literature," NDT Plus, 3:260-264, 2010.
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Lopatkin et al., "Efferent methods in medicine, M.," Medicine, pp. 266, 272-273, 276-279, 1989.
Low, R. et al., "Protein n, a primosomal DNA replication protein of *Escherichia coli*," Journal of Biological Chemistry, 257(11):6242-6250, 1982.
Mandal, "Sialic acid binding lectins," Experientia, 46:433-439, 1990.
Mariano et al., "Tailoring high-cut-off membranes and feasible application in sepsis-associated acute renal failure: in vitro studies," Nephrol Dial Transplant, 20:1116-1126, 2005.
Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6):659-664, 2011.
McGuigan et al., "Vancomycin (Vanocin)," Clinical Toxicology Review, 24(2):1-2, 2001.

(56) References Cited

OTHER PUBLICATIONS

Miao, J. et al., "Adsorption of doxorubicin on poly (methyl methacrylate)-chitosan-heparin coated activated carbon beads," Langmuir, 28(9):4396-4403, 2012.
Millen, H. et al., "Glass wool filters for concentrating waterborne viruses and agricultural zoonotic pathogens," J. Vis. Exp., 61:e3930, 2012.
Murphy, J.W. et al., "Structural and functional basis of CXCL 12 (stromal cell-derived factor-1 a) binding to heparin," Journal of Biological Chemistry, 282(13):10018-10027, 2007.
Nadkarni et al., Abstract of "Directional immobilization of heparin onto beaded supports," Anal. Biochem., 222(1):59-67, 1994.
Ofek et al., "Mannose binding and epithelial cell adherence of *Escherichia coli*," Infection and Immunity, 22(1):247-254, 1978.
Office Action mailed Jun. 23, 2020 in Japanese Patent Application No. 2017-515161, with English translation, retrieved from <https://globaldossier.uspto.gov/#/details/JP/2017515161/A/129021> on Aug. 13, 2020.
Ok, S. et al., "Emodin inhibits invasion and migration of prostate and lung cancer cells by downregulating the expression of chemokine receptor CXCR4," Immunopharmacology and Immunotoxicology, 34(5):768-778, 2012.
Park, P. et al., "Activation of Syndecan-1 ectodomain shedding by *Staphylococcus aureus* α-toxin and β-toxin," J. Biol. Chem., 279(1):251-258, 2004.
Popova et al., "Acceleration of epithelial cell syndecan-1 shedding by anthrax hemolytic virulence factors," BMC Microbiolgy, 6:8, pp. 1-16, 2006.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Riesenfeld et al., "Quantitative analysis of N-sulfated, N-acetylated, and unsubstituted glucosamine amino groups in heparin and related polysaccharides," Anal Biochem, 188:383-389, 1990.
Rosenbaum, J. et al., "Effect of hemoperfusion on clearance of Gentamicin, Cephalothin, and Clindamycin from plasma of normal dogs," Journal of Infectious Diseases, 136(6):801-804, 1977.
Sagnella et al., "Chitosan based surfactant polymers designed to improve blood compatibility on biomaterials," Colloids and Surfaces B: Biointerfaces, 42:147-155, 2005.
Salek-Ardakani, S. et al., "Heparin and heparan sulfate bind interleukin-10 and modulate its activity," Blood, 96:1879-1888, 2000.
Salmivirta, M. et al., "Neurite growth-promoting protein (Amphoterin, p30) binds syndecan," Experimental Cell Research, 200:444-451, 1992.
Sanaka, T. et al., "Continuous Arteriovenous Hemofiltration," Artificial Organs, 14(5):1822-1830, 1985.
Sanchez, J. et al., "Control of contact activation on end-point immobilized heparin: The role of antithrombin and the specific antithrombin-binding sequence," J. Bio. Mat. Res., 29:665-661, 1995.
Sasaki et al., Abstract: "Improved method for the immobilization of heparin," J. Chrom., 400:123-32, 1987.
Sato, T. et al., "Experimental study of extracorporeal perfusion for septic shock," Asaio Journal, 39(3):M790-M793, 1993.
Schefold et al., "A novel selective extracorporeal intervention in sepsis: immunoadsorption of endotoxin, interleukin 6, and complement-activating product 5A," Shock, 28(4):418-425, 2007.
Sharon, "Bacterial lectins, cell-cell recognition and infectious disease," FEBS letters, 217(2):145-157, 1987.
Slama, T., "Review: Gram-negative antibiotic resistance: there is a price to pay," Critical Care, 12(Suppl. 4):S4 (doi:10.1186/ccXXXX), May 21, 2008.
Smorenburg, S.M. et al., "The complex effects of heparins on cancer progression and metastasis in experimental studies," Pharmacological Reviews, 53(1):93-106, 2001.
Stevens, K. et al., "Hydrophilic surface coatings with embedded biocidal silver nanoparticles and sodium heparin for central venous catheters," Biomaterials, 32(5):1264-1269, 2011.
Swartz, "Recognition and management of anthrax—an update," New Engl. J. Med., 345(22):1621-1626, 2001.
Thomas et al., "Common oligosaccharide moieties inhibit the adherence of typical and atypical respiratory pathogens," Journal of Microbiology, 53:833-840, 2004.
Tonnaer, E. et al., "Involvement of glycosaminoglycans in the attachment of pneumococci to nasopharyngeal epithelial cells," Microbes and Infection, 8:316-322, 2006, available online Sep. 16, 2005.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Wadstrom, T. and A. Ljungh, "Glycosaminoglycan-binding microbial proteins in tissue adhesion and invasion: key events in microbial pathogenicity," J. Med. Microbiol., 48(3):223-233, 1999.
Wang, H. et al., "HMG-1 as a late mediator of endotoxin lethality in mice," Science, 285:248-251, 1999.
Ward et al., "Specificity of adsorption in a prototype whole blood affinity therapy device for removal of *Staphylococcus aureus*," Society for Biomaterials 2013 Annual Meeting and Exposition, Apr. 10, 2013, p. 1.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.
Weber et al., "Development of specific adsorbents for human tumor necrosis factor-α: influence of antibody immobilization on performance and biocompatibility," Biomacromolecules, 6:1864-1870, 2005.
Weir, D., "Carbohydrates as recognition molecules in infection and immunity," FEMS Microbiology Immunology, 47:331-340, 1989.
Wendel et al., "Coating-techniques to improve the hemocompatibility of artificial devices used for extracorporeal circulation," European Journal of Cardio-thoracic Surgery, 16:342-350, 1999.
Yu, J. et al., "Adhesion of coagulase-negative staphylococci and adsorption of plasma proteins to heparinized polymer surfaces," Biomaterials, 15(10):805-814, 1994.
Zhou et al., Abstract: "Heparin-agarose aqueous ethanol suspension," J. Mol. Bio., 271(3):12, 1997.
Chinese Patent Application No. 202080035938.0, Office Action, May 27, 2024, 17 pages (including English translation).
Maksimenko, A. and A. Turashev, "Endothelial glycocalyx of blood circulation. I. Detection, components, and structural organization," Russian Journal of Bioorganic Chemistry [Bioorganicheskaya Khimiya], 40(2): 131-41, 2014.

* cited by examiner

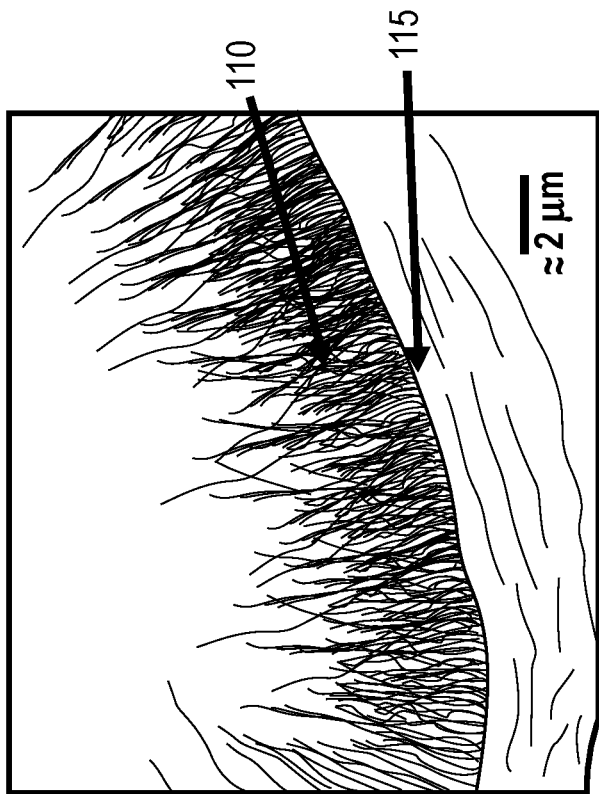
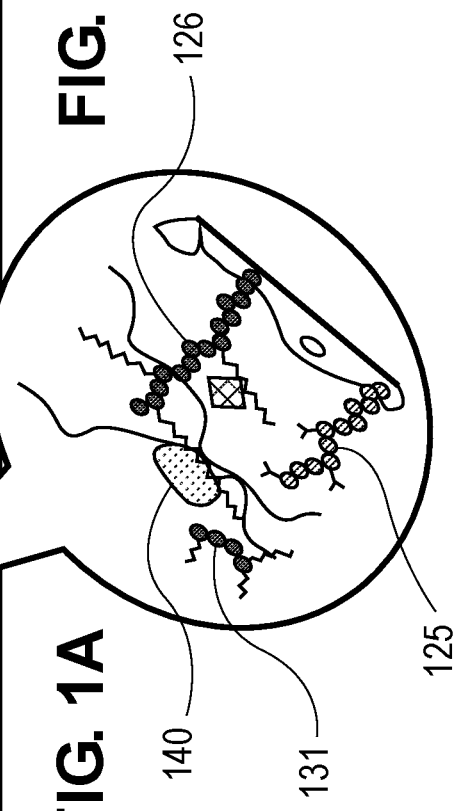
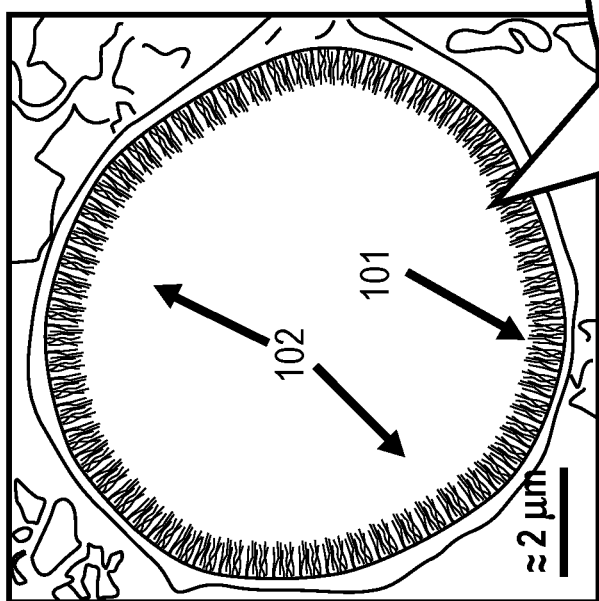
FIG. 1A
FIG. 1B
FIG. 1C

METHOD FOR MODULATING ENDOTHELIAL GLYCOCALYX STRUCTURE

CROSS-REFERENCES TO RELATED APPLICATIONS

The present application is a continuation of International Application No. PCT/US2020/032150, filed May 8, 2020, which claims priority to and benefit from U.S. Provisional Application No. 62/848,819, filed May 16, 2019, the entire contents of which are hereby incorporated by reference in its entity for all purposes.

BACKGROUND

Impairment of the glycocalyx barrier through structural damage or depletion, functional deficiency, or other mechanism may be a contributing cause of microvascular endothelial dysfunction, including inflammatory and coagulatory endothelial activation, vascular leakage of fluid, proteins, and other substances (e.g., cholesterol), failure to properly modulate perfused blood vessel density, and other deleterious conditions. All of the foregoing lead to general and specific negative vascular health indicators. For example, an unhealthy endothelial glycocalyx is associated with a "leaky" endothelium, which can be evidenced by (1) the presence (or "leakage") of cholesterol (or other substances, such as fluids, proteins, etc.) in (or into) the subendothelial space, and (2) a constricted lumen, which may reduce blood flow or perfusion into distal capillaries, muscles, organs, etc., increase blood pressure, and so forth. However, a healthy (thick and/or dense) endothelial glycocalyx is associated with a well-formed endothelium and healthy blood vessel structural configuration.

US 2020/0023001 to Ebong teaches compositions comprising heparan sulfate and sphingosine-1-phosphate for the regenerating endothelial glycocalyx and treating vascular disease. The exogenous heparan sulfate is incorporated into the glycocalyx.

Accordingly, there is a need for products, processes, and methods for treating (e.g., supporting and/or maintaining) the endothelial glycocalyx. The present disclosure provides these and other needs.

BRIEF SUMMARY

In general, provided herein are methods and devices for augmenting impaired glycocalyx barrier function in a subject in need thereof. In other words, the methods and devices described herein are for improving or repairing the functionality of a damaged or disrupted glycocalyx barrier in a subject. Consequently, methods and devices for treating a patient suffering from a disease associated with glycocalyx barrier dysfunction are also provided herein. A sample obtained from the subject with impaired glycocalyx barrier function is contacted with a glycocalyx-mimetic adsorption media. The adsorption media comprises structures and materials that are conducive to enhancing and/or restoring the impaired glycocalyx barrier function, acting as an artificial glycocalyx and removing from the sample the inflammatory mediators that would have been regulated by an undamaged or unimpaired glycocalyx barrier. The sample is subsequently separated from the adsorption media such that the impaired glycocalyx barrier function is augmented and/or the amount of inflammatory mediators in the now treated sample is reduced. This treated sample (e.g., blood) is then returned to the subject by reinfusion.

In one aspect, the present disclosure provides a method for augmenting impaired glycocalyx barrier function in a subject in need thereof. The method involves contacting a sample from the subject with a glycocalyx-mimetic adsorption media to enhance and/or restore the impaired glycocalyx barrier function, thereby treating the sample; and infusing the treated sample into the subject, wherein the glycocalyx-mimetic adsorption media is a solid substrate having an adsorbent, wherein the adsorbent is a glycosaminoglycan comprising heparin, or heparan sulfate, and mixtures thereof. The adsorbent does not leach from the solid substrate into the sample.

In one aspect, the adsorbent is a glycosaminoglycan mixture comprising from about 40% to about 96% w/w heparan sulfate and/or heparin, and, optionally, one or more of the following: from about 5% to about 30% w/w chondroitin sulfate, from about 1% to about 25% w/w dermatan sulfate, from about 0.01% to about 20% w/w keratan sulfate w/w, sialic acid/sialylated glycans, and/or from about 5% to about 50% w/w hyaluronic acid. In some embodiments, the glycosaminoglycan optionally comprises at least one proteoglycan core protein selected from the group consisting of syndecan, glypican, perlecan, versican, decorin, biglycan, and mimecan.

In some embodiments, the glycocalyx-mimetic adsorption media aids in a member selected from the group consisting of vascular permeability, adhesion of leucocytes, adhesion of platelets, mediation of shear stress, and modulation of an inflammatory process. In some embodiments, the adsorption media acts as an endothelial surface layer to protect and/or maintain glycocalyx function. In some embodiments, the adsorption media reduces a member selected from the group consisting of capillary leak syndrome, edema formation, inflammation, platelet hyperaggregation, hypercoagulation, and loss of vascular responsiveness.

In some embodiments, the adsorption media reduces shedding of the glycocalyx during reperfusion of a tissue. In some embodiments, the tissue is heart tissue during coronary by-pass surgery. In some embodiments, the tissue is perfused during an organ transplant.

In some embodiments, the adsorption media reduces shedding of the glycocalyx during sepsis. In some embodiments, the adsorption media removes tumor necrosis factor (TNF)-alpha and bacterial lipopolysaccharide (LPS). In some embodiments, the adsorption media reduces the risk of organ failure.

In some embodiments, the method treats acute respiratory distress syndrome (ARDS) in a subject.

In some embodiments, the method improves oxygen saturation in the subject.

In some embodiments, the method improves hemodynamic stability in the subject.

In some embodiments, the method treats Covid-19.

In some embodiments, the adsorption media reduces shedding of the glycocalyx resulting from atherosclerosis or diabetes. In some embodiments, the adsorption media removes low-density lipoproteins (LDL).

In some embodiments, the adsorption media binds heparin binding protein (HBP).

In some embodiments, the treated sample has a HBP content that is reduced by about 10% to about 100% compared to the HBP content of the sample prior to treatment.

In some embodiments, the adsorption media binds a member selected from the group consisting of exotoxins, endotoxins, ultra large von Willebrand factor (ULVWF), histones, exosomes, microvesicles and cytokines.

In some embodiments, the sample is a member selected from the consisting of whole blood, serum and plasma. In some embodiments, the sample is whole blood.

In some embodiments, the glycocalyx-mimetic adsorption media is negatively charged.

In some embodiments, the solid substrate comprises any non-toxic, non-leaching material. In some embodiments, the solid substrate comprises a plurality of rigid polymer bead. In some embodiments, the rigid polymer bead is selected from the group consisting of polyurethane, polymethylmethacrylate, polyethylene or co-polymers of ethylene and other monomers, polyethylene imine, polypropylene, and polyisobutylene. In some embodiments, the solid substrate comprises one or a plurality of hollow fibers.

Another aspect of the present disclosure relates to a device for augmenting impaired glycocalyx barrier function in a subject in need thereof. The device includes a cartridge having a glycocalyx-mimetic adsorption media disposed therein, the cartridge having a first endplate and a second endplate, and wherein the glycocalyx-mimetic adsorption media is a solid substrate having an adsorbent, wherein the adsorbent is a glycosaminoglycan mixture comprising heparin, heparan sulfate, or a mixture thereof. In some embodiments, the adsorbent of the device is a glycosaminoglycan mixture comprising from about 40% to about 96% w/w heparan sulfate and/or heparin, and, optionally, one or more of the following: from about 5% to about 30% w/w chondroitin sulfate, from about 1% to about 25% w/w dermatan sulfate, from about 0.01% to about 20% w/w keratan sulfate, sialic acid/sialylated glycans, and/or from about 5% to about 50% w/w hyaluronic acid; the device further comprising a sample influx port to allow sample to flow into the device; and a sample efflux port to allow sample to flow out of the device, wherein the sample flows through the first endplate through the adsorption media and out the sample efflux port. In some embodiments, the glycosaminoglycan mixture optionally comprises at least one proteoglycan core protein selected from the group consisting of syndecan, glypican, perlecan, versican, decorin, biglycan, and mimecan.

In some embodiments, the glycocalyx-mimetic adsorption media aids in a member selected from the group consisting of vascular permeability, adhesion of leucocytes, adhesion of platelets, mediation of shear stress, and modulation of an inflammatory process. In some embodiments, the adsorption media acts as an endothelial surface layer to protect and/or maintain glycocalyx function. In some embodiments, the adsorption media reduces a member selected from the group consisting of capillary leak syndrome, edema formation, inflammation, platelet hyperaggregation, hypercoagulation, and loss of vascular responsiveness.

In some embodiments, the glycocalyx-mimetic adsorption media is negatively charged.

In some embodiments, the solid substrate comprises any non-toxic, non-leaching material. In some embodiments, the solid substrate comprises a plurality of rigid polymer bead. In some embodiments, the rigid polymer bead is selected from the group consisting of polyurethane, polymethylmethacrylate, polyethylene or co-polymers of ethylene and other monomers, polyethylene imine, polypropylene, and polyisobutylene. In some embodiments, the solid substrate comprises one or a plurality of hollow fibers.

In yet another embodiment, the present disclosure provides method for improving oxygen saturation in a subject in need thereof. The method involves contacting a sample from the subject with a glycocalyx-mimetic adsorption media to enhance and/or restore the impaired glycocalyx barrier function, thereby treating the sample; and infusing the treated sample into the subject, wherein the glycocalyx-mimetic adsorption media is a solid substrate having an adsorbent, wherein the adsorbent is a glycosaminoglycan comprising heparin, heparan sulfate, or a mixture thereof.

These and other embodiments, aspects and objects will become more apparent when read with the detailed description together with the accompanying figures which follow.

BRIEF DESCRIPTION OF THE DRAWINGS

FIG. 1A shows a depiction of an electron micrograph of the glycocalyx.

FIG. 1B shows an enlarged view of a depiction of an electron micrograph of the glycocalyx.

FIG. 1C shows a depiction of an electron micrograph of the glycocalyx.

DETAILED DESCRIPTION

Figure 2A:
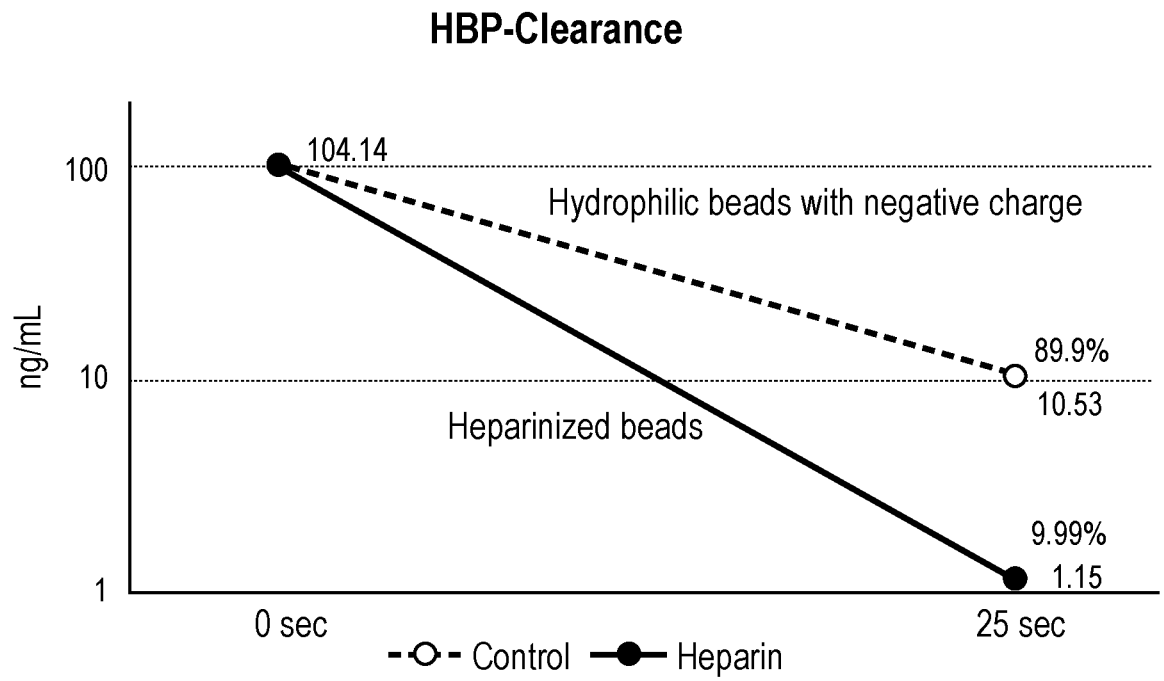
FIG. 2A shows that heparin binding protein (HBP) is adsorbed by heparin.

The present disclosure relates in part to methods and devices for augmenting, improving, and/or restoring the functionality of an impaired (or disrupted) glycocalyx barrier. Disruption and impairment of the glycocalyx is the cause of many disorders and diseases of the vascular system, such as, for example, sepsis and edema. The methods include the use of a glycocalyx-mimetic adsorption media, which acts as an artificial glycocalyx to remove many mediators of inflammation in a sample from a subject having impaired glycocalyx barrier function, thereby treating or "cleansing" the sample. The treated or "cleansed" sample can then be continuously or intermittently reinfused into the subject.

A technical advantage of the embodiments described herein is that the use of the glycocalyx-mimetic glycosaminoglycan adsorbent targets the cause of inflammatory and vascular disorders, rather than treating symptoms. Advantageously, the current methods restore the functionality of a damaged glycocalyx barrier in a safe and efficacious way.

I. DEFINITIONS

Unless defined otherwise, all technical and scientific terms used herein have the same meaning as commonly understood by one of ordinary skill in the art to which this disclosure belongs. As used herein the following terms have the following meanings.

As used herein, the terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

As used herein, the terms "comprising" or "comprises" are intended to mean that the compositions, devices, and methods include the recited elements, but do not exclude others. "Consisting essentially of" refers to those elements required for a given embodiment. The phrase permits the presence of additional elements that do not materially affect the basic and novel or functional characteristic(s) of the given embodiment (e.g., compositions, devices, and methods). "Consisting of" refers to compositions, devices, methods, and respective components thereof, as described herein, which are exclusive of any element not recited in that description of the embodiment. Embodiments defined by each of these transition terms are within the scope of this disclosure.

As used herein, the term "augmenting impaired glycocalyx barrier function" refers to potentiating or improving the function an endothelial glycocalyx barrier, which has been disrupted, damaged, or impaired. In a general sense, "augmenting" refers to the phenomenon in which the combination of two or more components provides an effect that is greater than the effect of the individual components or the sum of the components acting alone. Thus, in the context of the present disclosure, the combination of the glycocalyx-mimetic adsorption media with the damaged glycocalyx barrier with impaired function leads to the increased and improved performance of the impaired glycocalyx barrier function that is greater than performance of the impaired glycocalyx barrier function without the presence of adsorption media. For example, contacting a sample from a subject suffering from impaired glycocalyx barrier function with a glycocalyx-mimetic adsorption media of the instant disclosure augments or improves the impaired glycocalyx barrier function. In other words, being in contact with the adsorption media improves enhances and/or restores the impaired glycocalyx barrier function to an un-impaired or restored glycocalyx barrier function.

As used herein, the terms "glycocalyx barrier," "endothelial glycocalyx barrier," and "glycocalyx" are used interchangeably to refer to the carbohydrate-rich layer lining located at the interface between endothelial cells of the vascular endothelium and circulating blood. The glycocalyx is connected to the endothelium primarily through proteoglycans and glycoproteins, in which soluble plasma molecules are incorporated and linked to each other, either directly or through soluble proteoglycans and/or glycosaminoglycans. Thus, the glycocalyx composition is a dynamic mesh of interactions between the membrane-bound proteoglycans, glycoproteins, and glycosaminoglycans and the soluble glycosaminoglycans and plasma proteins. Endothelial function is primarily regulated through the glycocalyx as it mediates adhesion of platelets and leukocytes, hemostasis, and vascular barrier functions, and more, the details of which are described herein.

As used herein, the term "impaired glycocalyx barrier function" refers to a reduction in the ability of the glycocalyx barrier to shield the vascular walls from direct blood flow exposure. For example, the impaired glycocalyx barrier function can be the inability of the glycocalyx to serve as a vascular permeability barrier by losing its ability to: regulate coagulation, prevent adhesion of platelets to the vascular wall, prevent adhesion of leukocytes to the vascular wall, modulate shear stress to endothelial cells, and modulate inflammatory processes. "Disrupting" or "disruption of" the glycocalyx as used herein refers to any process or condition that affects the glycocalyx such that it is not functioning normally (i.e., impaired function). Disruption can be caused by inflammation or oxidation in the body. Disruption can cause the glycocalyx to thin (enzymatic or shear-induced shedding) and lose its component proteoglycans, resulting in a glycocalyx having impaired functionality. The following references describe various organ tissue models, animal models, clinical studies, and/or assays which demonstrate glycocalyx disruption and its impaired function: Schott, U. et al. *Scand J Trauma Recuse Emerg Med.* 2016, 24(48), 1-8; Becker, B. F., et al. *Cardiovascular Research,* 2010, 87, 300-310; Kolidrovi, H., et al. *Mediators of Inflammation,* 2014, 1-14; Vlahu, C. A. et al. *J. Am. Soc. Nephrol.* 2012, 23, 1900-1908; Yeo, T. W., et al. *Clinical Infectious Diseases,* 2019, ciz038, https://doi.org/10.1093/cid/ciz038; and Mulivor, A. W., et al. *Am J Physiol Heart Circ Physiol.* 2004, 286(5), H1672-80.

As used herein, the term "glycocalyx-mimetic adsorption media" refers to a material having a surface that is modified, functionalized, coated, etc. with a composition (i.e., adsorbent) which may differ from the exact general composition and structure of a glycocalyx barrier, but functions in a manner substantially similar to a naturally occurring glycocalyx barrier. In the context of the present disclosure, the glycocalyx-mimetic adsorption media is a solid substrate having an adsorbent which is a glycosaminoglycan mixture comprising heparin, heparan sulfate, and mixtures thereof. In certain aspects, glycosaminoglycan mixture comprises heparin, heparan sulfate, and mixtures thereof, and, optionally one or more additional glycosaminoglycans, such as, for example, chondroitin sulfate, dermatan sulfate, keratan sulfate, sialic acid/sialylated glycans, and/or hyaluronic acid. The glycosaminoglycan adsorbent mixture can optionally further include at least one proteoglycan core protein, such as, for example, syndecan, glypican, perlecan, versican, decorin, biglycan, mimecan, or a combination thereof. In other words, the glycocalyx-mimetic adsorption media is a solid substrate comprising a glycosaminoglycan adsorbent and functions as a natural glycocalyx barrier, which is capable of binding to analytes/adsorbates present in a sample, the details of which are described herein. The glycocalyx-mimetic adsorption media also acts as an endothelial surface layer to protect and/or maintain glycocalyx function, which, prior to contact with the glycocalyx-mimetic adsorption media, was impaired in function.

As used herein, the term "adsorbent" refers to a glycosaminoglycan mixture which is attached to (e.g., linked, coupled or bound) the solid substrate of the glycocalyx-mimetic adsorption media described herein. In certain instances, the adsorbent is the solid substrate itself. As such, the "glycosaminoglycan adsorbent" is a solid substrate with a glycosaminoglycan mixture attached thereto. For example, a glycosaminoglycan adsorbent is a polymer resin with a glycosaminoglycan mixture bound thereto. The glycosaminoglycan mixture includes heparin, heparan sulfate, and mixtures thereof, and, optionally, one or more additional glycosaminoglycans, such as, for example, chondroitin sulfate, dermatan sulfate, keratan sulfate, sialic acid/sialylated glycans, and/or hyaluronic acid. The glycosaminoglycan mixture can optionally further include at least one proteoglycan core protein, such as, for example, syndecan, glypican, perlecan, versican, decorin, biglycan, mimecan, or a combination thereof.

As used herein, the terms "analyte" and "adsorbate" are used interchangeably to refer to any molecule which disrupts glycocalyx barrier function and which has an affinity to the adsorbent. In the context of the present disclosure, a sample obtained from a subject suffering from impaired glycocalyx barrier function will contain adsorbates. When contacted with the glycocalyx-mimetic adsorption media of the present disclosure, the adsorbates bind to the surface of the adsorption media, and are thus removed from the sample. By disrupting the glycocalyx barrier function, these analytes promote or mediate inflammation, as well as other conditions and diseases associated with impaired glycocalyx barrier function. Non-limiting examples of adsorbates include, but are not limited to, the following inflammatory mediators: lymphokines, interferons, chemokines, exotoxins, endotoxins, ultra large von Willebrand factor (ULVWF), histones, exosomes, microvesicles, cytokines, tumor necrosis factor (TNF)-alpha, bacterial lipopolysaccharide (LPS), low-density lipoproteins (LDL), and heparin binding protein (HBP). For example, HIPB (i.e., azurocidin or CAP37) is stored in secretory vesicles and azurophilic granules of neutrophils and is released upon neutrophil adhesion and neutrophil extravasation during an inflammatory response. Bacterial products induce release of HBP leading to increased vascular leakage by acting on endothelial cells, in which HBP binds to the cell surface proteoglycans via heparan sulfate and chondroitin sulfate, thereby disrupting the glycocalyx and causing conditions associated with impaired glycocalyx barrier function (e.g., sepsis). See, e.g., Bentzer, P. et al. *Intensive Care Medicine Experimental*, 2016, 4(33), 1-16.

As used herein, the term "inflammation" refers to a protective response of tissue to injury or destruction in order to eliminate or cordon off any injurious agent and the injured tissue and initiate tissue repair. Inflammation can cause pain, heat, redness, swelling, and loss of function. Inflammatory mediators (e.g., lymphokines, interferons, chemokines, exotoxins, endotoxins, LDL, HBP) can cause shedding of the glycocalyx. Inflammation can also cause leukocytes to degranulate enzymes that can degrade the glycocalyx.

As used herein, the phrase "condition associated with impaired glycocalyx barrier function" refers to a human disease or condition that is at least in part caused by impaired glycocalyx barrier function or that induces impaired glycocalyx barrier function. Treating a condition associated with impaired glycocalyx barrier function, accordingly, refers to the treatment of the condition, recovering the impaired glycocalyx barrier function, or preventing or ameliorating conditions or symptoms arising from impaired glycocalyx barrier function, such as inflammation, intimal hyperplasia, and thrombosis. In the context of the present disclosure, augmenting impaired glycocalyx barrier function using the glycocalyx-mimetic adsorption media described herein can treat a condition associated with impaired glycocalyx barrier function. Non-limiting examples of conditions or diseases associated with impaired glycocalyx barrier function include: capillary leak syndrome, edema formation, inflammation, platelet hyperaggregation, hypercoagulation, loss of vascular responsiveness, sepsis, organ failure, atherosclerosis, and diabetes.

As used herein, the terms "glycosaminoglycan(s)," "GAG(s)," and "glycosaminoglycan chain(s)" are used interchangeably to refer to the glycan component of the glycosylated proteins (i.e., proteoglycans) that are present in endothelial glycocalyx. Generally, the proteoglycan structure includes a core protein with a plurality of covalently attached and/or interacting GAG chains with variable lengths. The glycosaminoglycans of the glycocalyx are structurally diverse, long, unbranched carbohydrate polymers of from about 5 to about 200,000, or more, repeating disaccharide units (e.g., from about 1 kDa to about 100,000 kDa, or more) and are negatively charged under physiological conditions. Each repeating disaccharide unit (i.e., "A-B") includes a hexose or a hexuronic acid (i.e., "A") glycosidically linked to a hexosamine (i.e., "B"), wherein the geometry of the glycosidic linkage can either be in the α or β configuration and each of the A and B components of every A-B unit can be independently modified or unmodified, the details of which are provided below. Non-limiting examples of GAGs which can be used in the embodiments described herein include chondroitin, chondroitin sulfate (CS), dermatan, dermatan sulfate (DS), heparan sulfate (HS), heparin, keratin, keratan sulfate, sialic acid/sialylated glycans, and hyaluronic acid (HA), the details of which are described herein. The "core proteins" of endothelial proteoglycans can either be bound directly to the endothelial cell membrane or exist in the glycocalyx as soluble plasma components. The endothelial proteoglycan core proteins vary in size (e.g., from about 20 kDa to about 500 kDa, or more) and in the number of attached GAG chains (e.g., from about 1 to about 50, or more, attached GAG chains). Accordingly, non-limiting examples of endothelial proteoglycan core proteins include syndecan, glypican, perlecan, versican, decorin, biglycan, and mimecan, the details of which are described herein. See, e.g., Reitsma, S., et al. *Pflugers Archiv: European Journal of Physiology*, 2007, 454, 345-359; Kolidrovi, H., et al. *Mediators of Inflammation*, 2014, 1-14.

As used herein, the term "A-B" refers to a single disaccharide unit of a glycosaminoglycan chain, in which "A" represents either a hexose or a hexuronic acid and "B" represents a hexosamine. In general, a disaccharide unit of the GAG chains described herein can include D-galactose (Gal), D-glucuronic acid (GlcA), or L-iduronic acid (IdoA) as component A, and D-galactosamine (GalN) or D-glucosamine (GlcN) as component B. The glycosidic linkages (i.e., C—O—C bonds) formed between the A and B component of an A-B unit (and between two or more A-B units, e.g., $-[A-B]_1-[A-B]_2-[A-B]_3-$) are covalent linkages formed from the hydroxyl groups of adjacent sugars. Linkages can occur between the 1-carbon and the 6-carbon of adjacent sugars (i.e., a 1-6 linkage, 1→6, or 1,6), the 1-carbon and the 4-carbon of adjacent sugars (i.e., a 1-4 linkage, 1→4, or 1,4), the 1-carbon and the 3-carbon of adjacent sugars (i.e., a 1-3 linkage, 1→3, or 1,3), or the 1-carbon and the 2-carbon of adjacent sugars (i.e., a 1-2 linkage, 1→2, or 1,2), the 2-carbon and the 4-carbon of adjacent sugars (i.e., a 2-4 linkage, 2→4, or 2,4), or the 2-carbon and the 3-carbon of adjacent sugars (i.e., a 2-3 linkage, 2→3, or 2,3). The GAG chains can also include linkages between carbon atoms other than the 1-, 2-, 3-, 4-, and 6-carbons.

A sugar component can be linked within a GAG such that the anomeric carbon is in the α- or β-configuration. In this regard, the glycosidic bond formed between the A and B component of an A-B unit can be referred to as either an α-link (or bond) or a β-linkage, with respect to the anomeric carbon configuration in A. The glycosidic bond formed between each disaccharide unit in a GAG chain can also be referred to as an α-bond or a β-bond (e.g., the bond between disaccharide $[A-B]_1$ and disaccharide $[A-B]_2$ in the $-[A-B]_1-[A-B]_2-$ chain may be an α-bond or a β-bond, with respect to the anomeric carbon configuration of $B_1$). For example, a GAG chain may contain a repeating disaccharide unit of $A_1\alpha(1\rightarrow 3)B_1$, wherein the 1-carbon of $A_1$ is in the a configuration and glycosidically linked to the 3-carbon of $B_1$. Disaccharide sequence $4A_1\alpha(1\rightarrow 3)B_1\beta 1$ indicates that the 4-carbon of $A_1$ is glycosidically linked to an undesignated carbon of the preceding adjacent sugar in the sequence and the 1-carbon of $B_1$ is in the R configuration and glycosidically linked to an undesignated carbon of the following adjacent sugar in the sequence.

Each A and/or B component of an A-B unit can be unmodified or can contain one or more modifications, such as O-sulfation and/or N-sulfation or N-acetylation, depending on the GAG polymer. In this regard, modifications of the hexose and hexuronic acid residues can include substituting one or more of the hydroxyl groups at the 2 position, 3 position, 4 position, and 6 position with an O-sulfate. Modifications of the hexosamine residues include substituting the amino group at the 2 position with either an N-acetyl or an N-sulfate, and/or substituting one or more of the hydroxyl groups at the 3 position, 4 position, and 6 position with an O-sulfate.

Examples of modified A components (i.e., hexose/hexuronic acid) include, but are not limited to, the following: Gal2S, containing an O-sulfate at the 2 position of D-galactose (Gal); Gal3S, containing an O-sulfate at the 3 position of D-galactose (Gal); Gal4S, containing an O-sulfate at the 4 position of D-galactose (Gal); Gal6S, containing an O-sulfate at the 6 position of D-galactose (Gal); GlcA2S, containing an O-sulfate at the 2 position of D-glucuronic acid (GlcA); GlcA3S, containing an O-sulfate at the 3 position of D-glucuronic acid (GlcA); GlcA4S, containing an O-sulfate at the 4 position of D-glucuronic acid (GlcA); GlcA6S, containing an O-sulfate at the 6 position of D-glucuronic acid (GlcA); IdoA2S, containing an O-sulfate at the 2 position of L-iduronic acid (IdoA); IdoA3S, containing an O-sulfate at the 3 position of L-iduronic acid (IdoA); IdoA4S, containing an O-sulfate at the 4 position of L-iduronic acid (IdoA); and IdoA6S, containing an O-sulfate at the 6 position of L-iduronic acid (IdoA).

Examples of modified B components (i.e., hexosamine), specifically, modifications to D-galactosamine (GalN), include, but are not limited to, the following: GalN3S, containing an O-sulfate at the 3 position of D-galactosamine (GalN); GalN4S, containing an O-sulfate at the 4 position of D-galactosamine (GalN); GalN6S, containing an O-sulfate at the 6 position of D-galactosamine (GalN); GalN3S6S, containing an O-sulfate at the 3 position and an O-sulfate at the 6 position of D-galactosamine (GalN); GalN3S4S, containing an O-sulfate at the 3 position and an O-sulfate at the 4 position of D-galactosamine (GalN); GalN4S6S, containing an O-sulfate at the 4 position and an O-sulfate at the 6 position of D-galactosamine (GalN); GalNAc (D-N-acetylgalactosamine), containing an N-acetyl at the 2 position of D-galactosamine (GalN); GalNAc3S, containing an O-sulfate at the 3 position of D-N-acetylgalactosamine (GalNAc); GalNAc4S, containing an O-sulfate at the 4 position of D-N-acetylgalactosamine (GalNAc); GalNAc6S, containing an O-sulfate at the 6 position of D-N-acetylgalactosamine (GalNAc); GalNAc3S6S, containing an O-sulfate at the 3 position and an O-sulfate at the 6 position of D-N-acetylgalactosamine (GalNAc); GalNAc3S4S, containing an O-sulfate at the 3 position and an O-sulfate at the 4 position of D-N-acetylgalactosamine (GalNAc); GalNAc4S6S, containing an O-sulfate at the 4 position and an O-sulfate at the 6 position of D-N-acetylgalactosamine (GalNAc); GalNS (D-N-sulfogalactosamine), containing an N-sulfate at the 2 position of D-galactosamine (GalN); GalNS3S, containing an O-sulfate at the 3 position of D-N-sulfogalactosamine (GalNS); GalNS4S, containing an O-sulfate at the 4 position of D-N-sulfogalactosamine (GalNS); GalNS6S, containing an O-sulfate at the 6 position of D-N-sulfogalactosamine (GalNS); GalNS3S6S, containing an O-sulfate at the 3 position and an O-sulfate at the 6 position of D-N-sulfogalactosamine (GalNS); GalNS3S4S, containing an O-sulfate at the 3 position and an O-sulfate at the 4 position of D-N-sulfogalactosamine (GalNS); and GalNS4S6S, containing an O-sulfate at the 4 position and an O-sulfate at the 6 position of D-N-sulfogalactosamine (GalNS).

Examples of modified B components (i.e., hexosamine), specifically, modifications to D-glucosamine (GlcN), include, but are not limited to, the following: GlcN3S, containing an O-sulfate at the 3 position of D-glucosamine (GlcN); GlcN4S, containing an O-sulfate at the 4 position of D-glucosamine (GlcN); GlcN6S, containing an O-sulfate at the 6 position of D-glucosamine (GlcN); GlcN3S6S, containing an O-sulfate at the 3 position and an O-sulfate at the 6 position of D-glucosamine (GlcN); GlcN3S4S, containing an O-sulfate at the 3 position and an O-sulfate at the 4 position of D-glucosamine (GlcN); GlcN4S6S, containing an O-sulfate at the 4 position and an O-sulfate at the 6 position of D-glucosamine (GlcN); GlcNAc (D-N-acetylglucosamine), containing an N-acetyl at the 2 position of D-glucosamine (GlcN); GlcNAc3S, containing an O-sulfate at the 3 position of D-N-acetylglucosamine (GlcNAc); GlcNAc4S, containing an O-sulfate at the 4 position of D-N-acetylglucosamine (GlcNAc); GlcNAc6S, containing an O-sulfate at the 6 position of D-N-acetylglucosamine (GlcNAc); GlcNAc3S6S, containing an O-sulfate at the 3 position and an O-sulfate at the 6 position of D-N-acetylglucosamine (GlcNAc); GlcNAc3S4S, containing an O-sulfate at the 3 position and an O-sulfate at the 4 position of D-N-acetylglucosamine (GlcNAc); GlcNAc4S6S, containing an O-sulfate at the 4 position and an O-sulfate at the 6 position of D-N-acetylglucosamine (GlcNAc); GlcNS (D-N-sulfoglucosamine), containing an N-sulfate at the 2 position of D-glucosamine (GlcN); GlcNS3S, containing an O-sulfate at the 3 position of D-N-sulfoglucosamine (GlcNS); GlcNS4S, containing an O-sulfate at the 4 position of D-N-sulfoglucosamine (GlcNS); GlcNS6S, containing an O-sulfate at the 6 position of D-N-sulfoglucosamine (GlcNS); GlcNS3S6S, containing an O-sulfate at the 3 position and an O-sulfate at the 6 position of D-N-sulfoglucosamine (GlcNS); GlcNS3S4S, containing an O-sulfate at the 3 position and an O-sulfate at the 4 position of D-N-sulfoglucosamine (GlcNS); and GlcNS4S6S, containing an O-sulfate at the 4 position and an O-sulfate at the 6 position of D-N-sulfoglucosamine (GlcNS). Therefore, GAG chains of the glycocalyx can contain a variety of different disaccharide units, in which each hexose/hexuronic acid residue and each hexosamine residue of every hexose/hexuronic acid-hexosamine pair (i.e., disaccharide unit) can be optionally independently mono- or multi-substituted (i.e., unmodified or modified).

As used herein, the terms "heparan sulfate" and "HS" are used interchangeably to refer to the glycosaminoglycan polymer of repeating disaccharide A-B units which can include GlcA, IdoA, and IdoA2S residues as possible A components, and GlcN, GlcNAc, GlcNAc6S, GlcNS, GlcNS6S, and GlcNS3S6S residues as possible B components. In general, heparan sulfate contains about 40-70% of non-sulfated disaccharide sequences, about 30-65% of various mono-sulfated disaccharide sequences, and about 1-10% of di- and/or tri-sulfated disaccharide sequences. Heparan sulfate polymers may have about 65 N-sulfates per every 100 disaccharide, an N-sulfation to O-sulfation ratio of about 2:3 to about 3:4, and an average of about 0.8 to about 1.8 sulfate groups per every disaccharide unit. The most prevalent disaccharide sequence in heparan sulfate is 4GlcAβ (1→4)GlcNAcα1, which may constitute up to about 50% or more of a HS chain. While GlcA is the more common hexuronic acid, IdoA may constitute about 30% to about 50% of heparan sulfate and may be present as the non-sulfated unit 4IdoAα(1→4)GlcNAcα1 and/or any mono-, di-, and/or tri-sulfated disaccharide units, such as, for example, 4IdoAα(1→4)GlcNSα1, 4IdoAα(1→4)GlcNAc6Sα1, and 4IdoAα(1→4)GlcNS6Sα1. Heparan sulfate polymers can have from about 20 to about 200, or more, repeating disaccharide units and can have a molecular weight of from about 10 kDa to about 100 kDa. See, e.g., Shriver, S. et al. *Handb. Exp. Pharmacol* 2012, 207, 159-176; Zhang, F. et al. Chapter 3—Glycosaminoglycans. 2010. In: Richard D. Cummings, J. Michael Pierce, et al., editors. Handbook of Glycomics, Academic Press, 2010, 59-80; Gandhi, N. et al *Chem. Biol. Drug Des.* 2008, 72, 455-482; Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the terms "heparin" and "Hep" are used interchangeably to refer to the glycosaminoglycan polymer of repeating disaccharide A-B units which can include GlcA, IdoA, and IdoA2S residues as possible A components, and GlcN, GlcNAc, GlcNAc6S, GlcNS, GlcNS6S, and GlcNS3S6S residues as possible B components. In general, heparin contains about 70-90% of tri-sulfated disaccharide sequences, about 10-30% of various non-, mono-, and di-sulfated disaccharide sequences, and an average of about 1.8 to about 2.8 sulfate groups per every disaccharide unit. The most prevalent disaccharide sequence in heparin is 4IdoA2Sα(1→4)GlcNS6Sα1, which may constitute up to about 70% or more of a Hep chain. Heparin polymers can have from about 15 to about 60, or more, repeating disaccharide units and can have a molecular weight of from about 10 kDa to about 35 kDa. Se, e.g., Shriver, S. et al. *Handb. Exp. Pharmacol.* 2012, 207, 159-176; Zhang, F. et al. Chapter 3—Glycosaminoglycans. 2010. In: Richard D. Cummings, J. Michael Pierce, et al., editors. Handbook of Glycomics, Academic Press, 2010, 59-80; Gandhi, N. et al. *Chem. Biol. Drug. Des.* 2008, 72, 455-482; Lindahl, U, et al Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the terms "chondroitin sulfate" and "CS" are used interchangeably to refer to the glycosaminoglycan polymer of repeating disaccharide A-B units which can include GlcA, GlcA2S, and GlcA3S residues as possible A components, and GalNAc, GalNAc4S, GalNAc6S, and GalNAc4S6S residues as possible B components. Various types of chondroitin sulfate exist, such as, CS-A, CS-C, CS-D, and CS-D. The CS-B subtype is known as dermatan sulfate, which is described in detail herein. In general, chondroitin sulfate type A contains repeating disaccharide units of 4GlcAβ(1→3)GalNAc4Sβ1, chondroitin sulfate type C contains repeating disaccharide units of 4GlcAβ(1→3)GalNAc6Sβ1, chondroitin sulfate type D contains repeating disaccharide units of 4GlcA2Sβ(1→3)GalNAc6Sβ1, and chondroitin sulfate type E contains repeating disaccharide units of 4GlcAβ(1→3)GalNAc4S6Sβ1. The chondroitin sulfate chains may be hybrid structures, containing more than one type of chondroitin disaccharide unit. In other words, a hybrid CS polymer may contain repeating disaccharide sequences of 4GlcAβ(1→3)GalNAc4Sβ1 (chondroitin sulfate A), 4GlcAβ(1→3)GalNAc6Sβ1 (chondroitin sulfate C), 4GlcA2Sβ(1→3)GalNAc6Sβ1 (chondroitin sulfate D), and/or 4GlcAβ(1→3)GalNAc4S6Sβ1 (chondroitin sulfate E) in any amount and combination thereof. As a non-limiting example, a hybrid chondroitin sulfate chain contains about 40-60% 4GlcAβ(1→3)GalNAc4Sβ1, about 40-60% 4GlcAβ(1→3)GalNAc6Sβ1, and, optionally, about 1-20% of various non-, di- and/or tri-sulfated disaccharide sequences such as, for example, 4GlcAβ(1→3)GalNAcβ1, 4GlcA2Sβ(1→3)GalNAc6Sβ1 and/or 4GlcAβ(1→3)GalNAc4S6Sβ1. Chondroitin sulfate polymers (non-hybrid or hybrid) can have from about 4 to about 155, or more, repeating disaccharide units and can have a molecular weight of from about 2 kDa to about 70 kDa, or more. See, e.g., Zhang, F. et al Chapter 3—Glycosaminoglycans. 2010. In: Richard D. Cummings, J. Michael Pierce, et al., editors. Handbook of Glycomics, Academic Press, 2010, 59-80; Gandhi, N. et at. *Chem. Biol. Drug. Des.* 2008, 72, 455-482; Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the terms "dermatan sulfate" and "DS" are used interchangeably to refer to the glycosaminoglycan polymer of repeating disaccharide A-B units which can include GlcA, IdoA, and IdoA2S residues as possible A components, and GalNAc, GalNAc4S, and GalNAc6S residues as possible B components. In general, dermatan sulfate contains about 70-95% of mono-sulfated disaccharide sequences, about 5-20% of di-sulfated disaccharide sequences, and about 1-10% of non-sulfated disaccharide sequences. The most prevalent disaccharide sequence in a DS polymer is 4IdoAα(1→3)GalNAc4Sβ1, which may constitute up to 80% or more of a DS chain. Dermatan sulfate polymers can have from about 20 to about 155, or more, repeating disaccharide units and can have a molecular weight of from about 10 kDa to about 70 kDa, or more. See, e.g., Zhang, F. et al. Chapter 3—Glycosaminoglycans. 2010. In: Richard D. Cummings, J. Michael Pierce, et al., editors. Handbook of Glycomics, Academic Press, 2010, 59-80; Gandhi, N. et al. *Chem. Biol. Drug. Des.* 2008, 72, 455-482; Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the terms "keratan sulfate" and "KS" are used interchangeably to refer to the glycosaminoglycan polymer of repeating disaccharide A-B units which can include Gal and Gal6S residues as possible A components, and GlcNAc and GlcNAc6S residues as possible B components. Keratan sulfate contains a mixture of about non-sulfated disaccharide sequence 3Galβ(1→4)GlcNAcβ1, mono-sulfated disaccharide sequence 3Galβ(1→4)GlcNAc6Sβ1, and di-sulfated disaccharide sequence 3Gal6Sβ(1→4)GlcNAc6Sβ1. Disaccharides within the repeating region of keratan sulfate may be fucosylated and N-acetylneuraminic acid caps the end of the chains. See, e.g., Stanley, P. et at. Structures Common to Different Glycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 14. KS polymers can have from about 10 to about 70, or more, repeating disaccharide units and can have a molecular weight of from about 5 kDa to about 30 kDa, or more. See, e.g., Zhang, F. et al. Chapter 3—Glycosaminoglycans. 2010. In: Richard D. Cummings, J. Michael Pierce, et al., editors. Handbook of Glycomics, Academic Press, 2.010, 59-80; Gandhi, N. et al. *Chem. Biol. Drug Des.* 2008, 72, 455-482; Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the terms "hyaluronic acid," "hyaluronan," "HA," and "hyaluronate" are used interchangeably to refer to the glycosaminoglycan polymer of repeating disaccharide A-B units which can include GlcA residues as possible A components and GlcNAc residues as possible B components. HA is the only non-sulfated GAG polymer and contains the repeating disaccharide sequence 4GlcAβ(1→3) GalNAcβ1. Hyaluronan can be purified from animal and non-animal sources. HA polymers can have from about 10 to about 100,000 repeating disaccharide units and can have a molecular weight of from about 4 kDa to about 20,000 kDa. See, e.g., Zhang, F. et al. Chapter 3—Glycosaminoglycans. 2010. In: Richard D. Cummings, J. Michael Pierce, et al., editors. Handbook of Glycomics, Academic Press, 2010, 59-80; Gandhi. N. et al. *Chem. Biol. Drug. Des.* 2008, 72, 455-482; Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "syndecan" refers to a membrane bound core protein of the glycocalyx, which is connected to the membrane via a membrane-spanning domain. There are four subtypes of the syndecan core protein, ranging from about 20 kDa to about 45 kDa. The syndecan proteoglycan core protein can contain about 5 or more HS and CS glycosaminoglycan chains, such as, for example, 2-3 HS chains or a mixture of 3-4 HS and 1-2 CS chains. Syndecans can exhibit the following functions: regulator of cell adhesion, migration and actin cytoskeletal organization, and control of ligand clearance from cell surface. See, e.g., Lindahl U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "glypican" refers to a membrane bound core protein of the glycocalyx, which is connected to the membrane via a glycosylphosphatidylinositol anchor. There are six subtypes of the glypican core protein, ranging from about 55 kDa to about 70 kDa. The glypican proteoglycan core protein can contain about 3 or more HS glycosaminoglycan chains. Glypicans can function as co-receptors regulating signaling through associated (e.g., tyrosine kinase receptors. See, e.g., Lindahl, U, et a. Proteoglycans and Sulfated Glycosaminoglycans. 2017. In: Varki A, Cummings R-D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "perlecan" refers to a secreted core protein, existing in the glycocalyx as a soluble plasma component. Perlecan proteoglycan core proteins have an average core mass of about 400 kDa and can contain about 3 or more HS glycosaminoglycan chains, and, in some cases, 1, 2, or more CS chains (e.g., 1-4 HS chains or a mixture of 1-3 HS and 0-2 CS chains). Perlecan can exhibit the following functions: extracellular matrix (ECM) assembly, regulated cell migration through integrin interactions, and sequestration of growth factors (e.g., FGFs). See, e.g., Lindahl, U, et al Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "versican" refers to a secreted core protein, existing in the glycocalyx as a soluble plasma component. Versican proteoglycan core proteins have an average core mass of about 370 kDa and can contain about 10-30 or more CS and DS glycosaminoglycan chains (e.g., a mixture of 5-15 CS and 10-20 DS chains). Versican is involved in multiple ECM interactions, regulation of inflammation, and cell adhesion and migration. See, e.g., Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "decorin" refers to a secreted core protein, existing in the glycocalyx as a soluble plasma component, and is a member of the small leucine-rich proteoglycan (SLRP) family. As an SLRP, decorin contains leucine-rich repeats flanked by cysteines in their central domain. Decorin proteoglycan core proteins have an average core mass of about 35-40 kDa and can contain at least 1 CS chain and/or at least 1 DS chain. Decorin regulates interstitial collagen fibrillogenesis and is involved in the inhibition of TGF-β signaling. See, e.g., Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "biglycan" refers to a secreted core protein of the SLRP family, existing in the glycocalyx as a soluble plasma component. Biglycan proteoglycan core proteins have an average core mass of about 36-40 kDa and can contain about 2 or more CS and DS chains. Biglycan is involved in collagen matrix assembly and activation of innate immune system. See, e.g., Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "mimecan" refers to a secreted core protein of the SLRP family, existing in the glycocalyx as a soluble plasma component. Mimecan proteoglycan core proteins have an average core mass of about 25-35 kDa and can contain about 2 or more KS chains. Mimecan is involved in collagen matrix assembly, bone formation, and corneal transparency. See, e.g., Lindahl, U, et al. Proteoglycans and Sulfated Glycosaminoglycans. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 17.

As used herein, the term "contacting" refers to the process of bringing into contact at least two distinct species such that they are touching or of immediate or local proximity. In the context of the instant disclosure, a sample from a subject suffering from impaired glycocalyx barrier function is contacted with a glycocalyx-mimetic adsorption media. As such, the analytes/adsorbates within this sample contact the glycocalyx-mimetic adsorption media. Once in contact with the glycocalyx-mimetic adsorption media, the analytes/adsorbates remain attached to the glycocalyx-mimetic adsorption media, thereby removing the analytes/adsorbates from the sample.

As used herein, the term "sample" refers to any biological sample that could contain an analyte/adsorbate obtained from a subject suffering from impaired glycocalyx barrier function. Typically, the sample is in liquid form or can be changed into a liquid form. Non-limiting examples of samples include whole blood, serum, and plasma. In the context of the instant disclosure, a sample that has not been contacted with glycocalyx-mimetic adsorption media is regarded as an "untreated sample." Accordingly, the untreated sample contains glycocalyx barrier function disrupting molecules (i.e., the analytes/adsorbates). A "treated sample" is a sample that has been contacted with glycocalyx-mimetic adsorption media. The treated sample will contain a reduced amount of the analytes/adsorbates and, thus, can be considered "cleansed" or "clean."

As used herein, the term "perfusion" refers to the passage of liquid (i.e., blood) over and/or through an organ, while the term "reperfusion" refers to the passage of liquid over an/or through an organ which was previously unperfused (e.g., an artery clamped during surgery to prevent passage of blood). Stated another way, reperfusion refers to the act of restoring the flow of blood to an organ or tissue (e.g., heart, kidney, etc.).

As used herein, the term "rigid polymer bead" refers to a bead, granule, pellet, sphere, particle, microcapsule, sphere, microsphere, nanosphere, microbead, nanobead, microparticle, nanoparticle, and the like that is made from a polymer resin or other biocompatible substrate material.

The term "percent weight," unless otherwise defined, means % or refers to the percentage of a component measured in weight per total weight of a particular composition. Percent weight is represented by "%" or "% w/w." In the context of the instant disclosure, a glycosaminoglycan adsorbent (e.g., glycosaminoglycan mixture) that is attached to the solid substrate of the glycocalyx-mimetic adsorption media described herein will contain particular amounts of GAG chains, and, in some cases, particular amounts of proteoglycan core proteins, which are based on the total weight of the glycosaminoglycan mixture. As such, the % w/w of each GAG chain (and optional one or more core protein) in the adsorption media is based on the total weight of the glycosaminoglycan mixture that is used to coat or functionalize the surface of the solid substrate.

II. METHODS AND DEVICES

Disclosed herein are materials, compounds, compositions, and components that can be used for, can be used in conjunction with, can be used in preparation for, or are products of the disclosed methods, compositions, and devices. These and other materials are disclosed herein, and it is understood that when combinations, subsets, interactions, groups, etc. of these materials are disclosed that while specific reference of each various individual and collective combinations and permutation of these materials may not be explicitly disclosed, each is specifically contemplated and described herein. For example, if a method, composition, or device is disclosed and a number of modifications that can be made to a number of components of the method, composition, or device are discussed, each and every combination and permutation that are possible are specifically contemplated unless specifically indicated to the contrary.

Thus, if a class of components or elements A, B, and C are disclosed as well as a class of components or elements D, E, and F and an example of a method, composition, or device A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions and devices. Thus, if there are a variety of additional steps that can be performed, it is understood that each of these additional steps can be performed with any specific aspect or combination of aspects of the disclosed methods, and that each such combination is specifically contemplated and should be considered disclosed.

FIG. 1A-C show an electron micrograph of the glycocalyx. As shown in FIG. 1A and the inset, the glycocalyx 101 is a slippery, gel-like network of negatively charged molecules residing on the luminal side of the vascular endothelium. The lumen of the vessel is shown as 102. FIG. 1B is an enlargement and shows that the negatively charged glycocalyx consists of a web of membrane-bound glycoproteins 126, 131, 140 and proteoglycans 125 that are associated with a variety of glycosaminoglycans. It is cooperatively connected to the vascular endothelium by a host of backbone molecules (primarily the aforementioned proteoglycans and glycoproteins) forming a network in which a variety of water-soluble molecules is incorporated. The glycosaminoglycan is able to bind water up to 10,000× its own weight, thus making a major contribution to the overall volume of the endothelial glycocalyx.

FIG. 1C shows that the glycocalyx 110 is a carbohydrate-rich layer connected to the endothelium 115 via backbone proteoglycans and glycoproteins. A complex network of plasma- and epithelium-derived soluble molecules is continuously incorporated in the glycocalyx. A dynamic equilibrium forms between blood constituents and the glycocalyx (See, C. Biddle, AANA Journal, 81, (6) (2013).

The present disclosure provides a method for augmenting impaired glycocalyx barrier function in a subject in need thereof. The method involves contacting a sample from the subject with a glycocalyx-mimetic adsorption media to enhance and/or restore the impaired glycocalyx barrier function, thereby treating the sample; and infusing the treated sample into the subject, wherein the glycocalyx-mimetic adsorption media is a solid substrate having an adsorbent, wherein the adsorbent is a glycosaminoglycan mixture comprising at least one glycosaminoglycan (GAG) chain, and, optionally, one or more proteoglycan core proteins.

The impaired glycocalyx barrier function can be the result of an altered, disrupted, or damaged glycocalyx barrier structure or composition. Located on the apical surface of vascular endothelial cells which line the lumen, the glycocalyx is a negatively charged dynamic network of proteoglycans, glycoproteins, and glycolipids, with of a wide range of enzymes and proteins that regulate cellular and molecular adhesion and transport. A principal role of the glycocalyx in the vasculature is to maintain plasma and vessel wall homeostasis. Enzymes and proteins as well as other molecular entities serve to reinforce the glycocalyx barrier against vascular and other diseases. Another function of the glycocalyx within the vascular endothelium is to shield the vascular walls from direct exposure to blood flow, while serving as a vascular permeability barrier. Thus, the shear generated by blood flow regulates the balance between biosynthesis and shedding of the various glycocalyx components. Its protective functions are universal throughout the vascular system, with its relative importance varying depending on its exact location in the vasculature. The glycocalyx is involved in the filtration of fluid from the plasma to the interstitial space, protection of the endothelium from blood cell adhesion, mediation of the signal for nitric oxide (NO) production by endothelial cells. As a result, the glycocalyx serves as a protective barrier for the important vascular systems such as the brain, spinal cord, organs, lungs and lymphatic system. Thus, alteration or damage of this complex and dynamic glycocalyx barrier structure ultimately results in impaired glycocalyx barrier function, rendering the vascular systems susceptible to injury and disease.

The subject suffering from impaired glycocalyx barrier function can be an animal. In some embodiments, the subject is a mammal. In some embodiments, the subject is a human. The subject can be of any gender or age. In some embodiments, the subject suffering from impaired glycocalyx barrier function has one or more of the following conditions: capillary leak syndrome, edema formation, inflammation, platelet hyperaggregation, hypercoagulation, loss of vascular responsiveness, sepsis, organ failure, atherosclerosis, and diabetes.

The sample from the subject can be any bodily fluid taken from the subject. In some embodiments, the sample comprises whole blood. In some embodiments, the sample comprises serum. In some embodiments, the sample comprises plasma. In some embodiments, the sample comprises cerebrospinal fluid. The sample can be taken from the subject in the form of a discrete sample to be treated with the method. The sample can be taken from the subject in the form a continuous or semi-continuous stream. The amount of sample that can be used in the claimed methods is not intended to be limited. It can range from less than 1 mL to above 1 L, up to and including the entire blood volume of the subject when the sample comprises blood and when continuous recirculation back to the subject is employed. One or more 'passes' through the adsorption bed may be used if needed. The term "adsorption bed" refers to a container, chamber, column, etc. which holds the glycocalyx-mimetic adsorption media. The adsorption bed may be part of a dialysis or extracorporeal circuit. In other aspects, it can be part of a blood bag.

In some embodiments, the sample is taken from the subject at a rate of about 5 mL/min, about 10 mL/min, about 15 mL/min, about 20 mL/min, about 25 mL/min, about 30 mL/min, about 35 mL/min, about 40 mL/min, about 45 mL/min, about 50 mL/min, about 60 mL/min, about 70 mL/min, about 80 mL/min, about 90 mL/min, about 100 mL/min, about 150 mL/min, about 200 mL/min, about 250 mL/min, about 300 mL/min, about 350 mL/min, about 400 mL/min, about 450 mL/min, about 500 mL/min, about 550 mL/min, about 600 mL/min, about 700 mL/min, about 800 mL/min, about 900 mL/min, about 1000 mL/min, or even about 2000 to 6000 mL/min.

The glycocalyx-mimetic adsorption media of the present disclosure are designed to function similarly to a naturally occurring glycocalyx barrier having un-impaired functionality. As such, the glycocalyx-mimetic adsorption media augments, enhances, improves, and/or potentiates the ability of the damaged/dysfunctional endothelial glycocalyx barrier to function properly. In other words, contacting the sample from the subject suffering from impaired glycocalyx barrier function with a glycocalyx-mimetic adsorption media augments the impaired glycocalyx barrier function. In some embodiments, augmenting impaired glycocalyx barrier function through contact with the glycocalyx-mimetic adsorption media enhances or restores the ability of the damaged glycocalyx to: regulate coagulation, prevent adhesion of platelets to the vascular wall, prevent adhesion of leukocytes to the vascular wall, modulate shear stress to endothelial cells, and modulate inflammatory processes.

The sample from the subject suffering from impaired glycocalyx barrier function can be contacted with the glycocalyx-mimetic adsorption media for any length of time sufficient to augment, enhance, improve, and/or restore the impaired glycocalyx barrier function of the sample. In some embodiments, the sample contacts the glycocalyx-mimetic adsorption media for a duration of from 1 minute to 12 hours, or longer. In some embodiments, the sample is in contact with the glycocalyx-mimetic adsorption media for a duration of 1 minute, 5 minutes, 15 minutes, 20 minutes, 25 minutes, 30 minutes, 45 minutes, 60 minutes, 2 hours, 4 hours, 6 hours, 8 hours, 10 hours, or 12 hours. In some embodiments, the sample contacts the glycocalyx-mimetic adsorption media as an unbroken or contiguous stream, wherein the sample continuously flows over, on, or through the glycocalyx-mimetic adsorption media. The continuous-flow of a sample includes a constant or variable fluid flow having a set velocity or rate at which the sample is in contact with the glycocalyx-mimetic adsorption media. In some embodiments, the sample is in contact with the glycocalyx-mimetic adsorption media at a rate of about 5 mL/min, about 10 mL/min, about 15 mL/min, about 20 mL/min, about 25 mL/min, about 30 mL/min, about 35 mL/min, about 40 mL/min, about 45 mL/min, about 50 mL/min, about 60 mL/min, about 70 mL/min, about 80 mL/min, about 90 mL/min, about 100 mL/min, about 150 mL/min, about 200 mL/min, about 250 mL/min, about 300 mL/min, about 350 mL/min, about 400 mL/min, about 450 mL/min, about 500 mL/min, about 550 mL/min, about 600 mL/min, about 700 mL/min, about 800 mL/min, about 900 mL/min, or about 1000 mL/min.

The sample from the subject suffering from impaired glycocalyx barrier function can be contacted with the glycocalyx-mimetic adsorption media one or more times to augment, enhance, improve, and/or restore the impaired glycocalyx barrier function of the sample. In some embodiments, the sample contacts the glycocalyx-mimetic adsorption media at least once. In some embodiments, the sample contacts the glycocalyx-mimetic adsorption media 1 to 20 times, or more. In some embodiments, the sample contacts the glycocalyx-mimetic adsorption media 1 time, 2 times, 3, 4, 5, 6, 7, 8, 9, 10, 11, 12, 13, 14, or 15 times.

The glycocalyx-mimetic adsorption media for augmenting impaired glycocalyx barrier function of the sample and treating the sample can be a microporous media such as activated carbon or size exclusion chromatography resin that has been rendered blood compatible. In some embodiments, the glycocalyx-mimetic adsorption media does not contain activated carbon. The glycocalyx-mimetic adsorption media can be in a vessel such as a column, cartridge, tube, centrifuge tube, bottle, flexible bag, and the like, or any vessel wherein the treated sample can be removed without disturbing the glycocalyx-mimetic adsorption media.

Various materials, in shape and composition, can be used as the solid substrate of the glycocalyx-mimetic adsorption media in the methods and devices of the instant disclosure.

All suitable solid substrates provide high surface area while promoting the conveyance of adsorbates to the adsorbent sites that bind them (primarily) by forced convective or diffusion transport, thereby augmenting the impaired glycocalyx barrier function. Useful solid substrates for creating the glycocalyx-mimetic adsorption media include non-porous rigid beads, particles or packing, reticulated foams, a rigid monolithic bed (e.g. formed from sintered beads or particles), a column packed with woven or non-woven fabric, a column packed with a yarn or solid or hollow mesoporous or microporous monofilament fibers, a spiral wound cartridge formed from flat film or dense membrane, or a combination of media such as a mixed bead/fabric cartridge. In some embodiments, the solid substrate is one that is initially mesoporous or microporous, but becomes essentially non-porous when the surface is treated before, during, or after the creation of adsorption sites. In some embodiments, the substrate includes a polymer or rigid polymer bead. The substrate can also be metal, ceramic, glass, natural mineral, silica, and the like. Typically, the substrate does not leach impurities that cause clinically significant problems if they enter the patient's blood.

In some embodiments, the total surface area of the solid substrate can be in the range of 0.1-10,000 square meters, preferably in the range of 0.5-50 square meters, such as 0.5, 1, 1, 2, 2, 5, 10, 25, 40 and 50 square meters and numerical values between these. In some embodiments, the material of the solid substrate is selected from the group consisting of glass, silica, latex, cellulose, cellulose acetate, chitin, chitosan, cross-linked dextran, cross-linked agarose, cross linked alginate, polyethylene, polypropylene, polystyrene, polycarbonate, polysulfone, polyacrylonitrile, silicone, fluoropolymers (such as polytetrafluoroethylene), polyurethanes, and other synthetic polymers. Other materials commonly used for medical applications may also be employed. In some embodiments, the solid substrate comprises a cross-linked polysaccharide. The solid substrate can comprise a plurality of adsorbent monolayers, filters, membranes, solid fibers, hollow fibers, particles, or beads. Optionally, the solid substrate can be present in other forms or shapes providing a large surface area.

In some embodiments, the solid substrate is a mixed media solid substrate created by layering different glycocalyx-mimetic adsorption media of the solid substrate in a parfait-type arrangement such that the sample contacts the different media in series or parallel flow. Certain mixed media embodiments are disclosed in U.S. Pat. No. 8,758,286, incorporated herein by reference. One arrangement of the different media is to position unblended glycocalyx-mimetic adsorption media (i.e., anionic media) at the fluidic entrance and/or the fluidic exit regions of the solid substrate, with an optionally blended region comprising other materials interposed between the entrance and exit regions such as a cationic media. In the case of media in fiber form, a mixed woven, knitted, or nonwoven structure can be prepared by methods well known in the textile industry to form fabric from the mixed fiber. In some embodiments, a yarn is prepared from finer multifilament yarn or monofilament made from two or more fibers with different surface chemistries, wherein one fiber type contains a surface that actively prevents blood clotting on contact. This mixed-fiber yarn can then be used to prepare fabric suitable for a sample (e.g. blood) to contact.

The solid substrate of the glycocalyx-mimetic adsorption media is modified, functionalized, coated, etc. with an adsorbent, wherein the adsorbent is a glycosaminoglycan mixture comprising at least one glycosaminoglycan (GAG) chain. In some embodiments, the solid substrate of the glycocalyx-mimetic adsorption media is modified, functionalized, coated, etc. with a glycosaminoglycan adsorbent, wherein the adsorbent is a glycosaminoglycan mixture comprising at least one glycosaminoglycan (GAG) chain, and, optionally, one or more proteoglycan core proteins. In some embodiments, the solid substrate of the glycocalyx-mimetic adsorption media is modified, functionalized, coated, etc. with a glycosaminoglycan adsorbent, wherein the adsorbent is a glycosaminoglycan mixture comprising heparin, heparan sulfate, and mixtures thereof. In some embodiments, the glycosaminoglycan mixture adsorbent optionally further comprises one or more of the following: chondroitin sulfate, dermatan sulfate, keratan sulfate, sialic acid/sialylated glycans, and/or hyaluronic acid. In some embodiments, the glycosaminoglycan mixture comprises heparan sulfate, chondroitin sulfate, dermatan sulfate, keratan sulfate, sialic acid, sialylated glycans, and hyaluronic acid. In some embodiments, the glycosaminoglycan mixture comprises heparan sulfate, chondroitin sulfate, dermatan sulfate, keratan sulfate, sialic acid, and hyaluronic acid. In some embodiments, the glycosaminoglycan mixture comprises heparan sulfate, chondroitin sulfate, dermatan sulfate, keratan sulfate, sialylated glycans, and hyaluronic acid. In some embodiments, the glycosaminoglycan mixture comprises heparan sulfate, chondroitin sulfate, dermatan sulfate, keratan sulfate, and hyaluronic acid. In some embodiments, the glycosaminoglycan mixture consists essentially of heparan sulfate, chondroitin sulfate, dermatan sulfate, keratan sulfate, and hyaluronic acid. In some embodiments, the solid substrate of the glycocalyx-mimetic adsorption media is modified, functionalized, coated, etc. with an adsorbent, wherein the adsorbent is a glycosaminoglycan mixture comprising from about 30% to about 98% w/w heparan sulfate, and, optionally, one or more of the following: from about 0.1% to about 50% w/w chondroitin sulfate, from about 0.1% to about 50% w/w dermatan sulfate, from about 0.001% to about 40% w/w keratan sulfate, and/or from about 0.1% to about 60% w/w hyaluronic acid. In some embodiments, the glycosaminoglycan mixture comprises from about 30% to about 98% w/w heparan sulfate, from about 0.1% to about 50% w/w chondroitin sulfate, from about 0.1% to about 50% w/w dermatan sulfate, from about 0.001% to about 40% w/w keratan sulfate, and from about 0.1% to about 60% w/w hyaluronic acid.

In some embodiments, the adsorbent is 100% heparin. In certain aspects, the adsorbent is 100% heparan sulfate. In certain aspects, the adsorbent is from 99% to 1% heparin and from 1% to 99% heparan sulfate.

In some embodiments, the glycosaminoglycan adsorbent containing about 30% to about 98% w/w heparan sulfate may also contain heparin. In certain instances, heparin can be used or substituted in lieu of heparan sulfate at any percentage thereof. For example, if the glycosaminoglycan mixture (i.e., the glycosaminoglycan adsorbent of the glycocalyx-mimetic adsorption media) contains 50% w/w heparan sulfate, any amount of the HS (e.g., from about 1% up to 50%, or from about 25% to 50%, or 50%, etc.) can be substituted with heparin. Thus, in certain instances, the adsorption media contains about 30% to about 98% w/w heparin in lieu of any heparan sulfate. In some embodiments, the adsorption media contains about 30% to about 98% w/w heparin-heparan sulfate mixture. In some embodiments, the heparin polymers comprise from about 15 to about 60 repeating disaccharide units, such as, for example, about 16, 17, 18, 20, 22, 24, 26, 28, 30, 32, 34, 36, 38, 40, 44, 48, 50, 52, 56, or about 60 repeating disaccharide units.

In some embodiments, the heparin polymers have a mean molecular weight within the range of from about 10 kDa to about 35 kDa, such as, for example, about 11 kDa, or about 12, 14, 16, 18, 20, 22, 24, 26, 28, 30, 32, or about 34 kDa.

In some embodiments, the glycosaminoglycan adsorbent can include one or more proteoglycan core proteins to which the GAG chains of the glycosaminoglycan mixture are covalently attached. Alternatively, or additionally, the glycosaminoglycan adsorbent can include one or more proteoglycan core proteins and the GAG chains of the glycosaminoglycan mixture, wherein the GAG chains are not covalently attached to the one or more proteins. The one or more core proteins can be syndecan, glypican, perlecan, versican, decorin, biglycan, mimecan, or a combination thereof. The glycosaminoglycan mixture adsorbent can have from about 0.001% to about 50% w/w of one or more core proteins. In some embodiments, the amount of one or more core proteins included in the glycosaminoglycan mixture ranges from about 0.001% to about 30% w/w, or from about 0.001% to about 5% w/w, about 0.05% to about 10% w/w, about 1% to about 15% w/w, or from about 5% to about 20% w/w. In some embodiments, the amount of one or more core proteins included in the glycosaminoglycan mixture is about 0.0015% w/w, or about 0.002%, 0.0025%, 0.005%, 0.0075%, 0.01%, 0.025%, 0.05%, 0.075%, 0.1%, 0.25%, 0.5%, 0.75%, 1.0%, 1.25%, 1.5%, 2.0%, 3.0%, 4.0%, 5.0%, 6.0%, 7.0%, 8.0%, 9.0%, 10.0%, 12.0%, 14.0%, 15.0%, 18.0%, 20.0%, 22.0%, 24.0%, or about 25.0% w/w. As such, in some embodiments, the adsorbent of the glycocalyx-mimetic adsorption media solid substrate optionally comprises one or more core proteins selected from the group consisting of syndecan, glypican, perlecan, versican, decorin, biglycan, mimecan, or a combination thereof, in an amount ranging from about 0.001% to about 50% w/w in addition to from about 30% to about 98% w/w heparan sulfate and one or more of the following: from about 0.1% to about 50% w/w chondroitin sulfate; from about 0.1% to about 50% w/w dermatan sulfate; from about 0.001% to about 40% w/w keratan sulfate; and from about 0.1% to about 60% w/w hyaluronic acid. In some embodiments, the glycosaminoglycan adsorbent does not contain one or more core proteins.

In some embodiments, the heparan sulfate polymers of the adsorbent comprise from about 20 to about 250 repeating disaccharide units. In some embodiments, the heparan sulfate polymers comprise about 20 repeating disaccharide units, or about 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, or about 250 repeating disaccharide units. In some embodiments, the heparan sulfate polymers of the glycosaminoglycan adsorbent comprise from about 22 to about 240 repeating disaccharide units. In some embodiments, the heparan sulfate polymers of the glycosaminoglycan adsorbent comprise about 24 repeating disaccharide units, about 60 repeating disaccharide units, about 80 repeating disaccharide units, about 120 repeating disaccharide units, or about 240 repeating disaccharide units.

In some embodiments, the heparan sulfate polymers of the adsorbent have a mean molecular weight within the range of from about 10 kDa to about 100 kDa. In some embodiments, the mean molecular weight of the heparan sulfate polymer is about 10 kDa, or about 15, 20, 25, 30, 35, 40, 45, 50, 55, 60, 65, 70, 75, 80, 85, 90, 95, or about 100 kDa. In some embodiments, the heparan sulfate polymers of the glycosaminoglycan adsorbent have a mean molecular weight of from about 10 kDa to about 98 kDa. In some embodiments, the heparan sulfate polymers of the adsorbent have a mean molecular weight of about 12 kDa, about 35 kDa, about 50 kDa, or about 85 kDa.

In some embodiments, the amount of heparan sulfate included in the adsorbent solid substrate of the glycocalyx-mimetic adsorption media ranges from about 40% to about 96% w/w. In some embodiments, the amount of heparan sulfate of the adsorbent is about 40% w/w, about 45%, about 50%, about 55%, about 60%, about 65%, about 70%, about 75%, about 80%, about 85%, about 90%, about 95%, or about 96% w/w. In some embodiments, the amount of heparan sulfate of the adsorbent ranges from about 50% to about 90% w/w. In some embodiments, the amount of heparan sulfate of the adsorbent ranges from about 55% to about 85% w/w.

In some embodiments, the chondroitin sulfate polymers of the adsorbent comprise from about 4 to about 155 repeating disaccharide units. In some embodiments, the chondroitin sulfate polymers comprise about 6 repeating disaccharide units, or about 8, 10, 12, 15, 18, 20, 22, 25, 30, 35, 40, 45, 50, 55, 60, 65, 70, 75, 80, 85, 90, 95, 100, 105, 110, 115, 120, 125, 130, 135, 140, 145, 150, or about 155 repeating disaccharide units. In some embodiments, the chondroitin sulfate polymers of the glycosaminoglycan adsorbent comprise from about 4 to about 152 repeating disaccharide units. In some embodiments, the chondroitin sulfate polymers of the glycosaminoglycan adsorbent comprise about 4 repeating disaccharide units, about 50 repeating disaccharide units, about 54 repeating disaccharide units, about 110 repeating disaccharide units, or about 148 repeating disaccharide units.

In some embodiments, the chondroitin sulfate polymers of the adsorbent have a mean molecular weight within the range of from about 2 kDa to about 70 kDa. In some embodiments, the mean molecular weight of the chondroitin sulfate polymer is about 4 kDa, or about 6, 8, 10, 12, 14, 15, 20, 25, 30, 35, 40, 45, 50, 55, 60, 65, or about 70 kDa. In some embodiments, the chondroitin sulfate polymers of the glycosaminoglycan adsorbent have a mean molecular weight of from about 2 kDa to about 68 kDa. In some embodiments, the chondroitin sulfate polymers of the adsorbent have a mean molecular weight of about 2 kDa, about 25 kDa, about 50 kDa, or about 70 kDa.

In some embodiments, the amount of chondroitin sulfate included in the adsorbent solid substrate of the glycocalyx-mimetic adsorption media ranges from about 5% to about 30% w/w. In some embodiments, the amount of chondroitin sulfate of the adsorbent is about 5%, about 7%, about 10% w/w, about 12%, about 15% w/w, about 18%, about 20% w/w, about 22% w/w, about 25% w/w, about 27% w/w, or about 30% w/w. In some embodiments, the amount of chondroitin sulfate of the adsorbent ranges from about 10% to about 24% w/w. In some embodiments, the amount of chondroitin sulfate of the adsorbent ranges from about 12% to about 22% w/w.

In some embodiments, the ratio of heparan sulfate to chondroitin sulfate of the adsorbent solid substrate of the glycocalyx-mimetic adsorption media can range from about 10:1 to about 1:10. In some embodiments, the ratio of heparan sulfate to chondroitin sulfate can range from about 8:1 to about 1:8, about 6:1 to about 1:6, or about 4:1 to about 1:4. In some embodiments, the ratio of heparan sulfate to chondroitin sulfate can be about 5:1, 5:2, 5:3, 5:4, 5:5, 4:5, 3:5, 2:5, or about 1:5. In some embodiments, the ratio of heparan sulfate to chondroitin sulfate can be about 4:1, 2:1, 4:3, 1:1, 3:4, 1:2, or 1:4. In some embodiments, the ratio of heparan sulfate to chondroitin sulfate can be about 6:1, 5:1, 4:1, 3:1, 2:1, or about 1:1. In some embodiments, the ratio of heparan sulfate to chondroitin sulfate is about 4:1.

In some embodiments, the dermatan sulfate polymers of the adsorbent comprise from about 20 to about 155 repeating disaccharide units. In some embodiments, the dermatan sulfate polymers comprise about 20 repeating disaccharide units, or about 22, 25, 30, 35, 40, 45, 50, 55, 60, 65, 70, 75, 80, 85, 90, 95, 100, 105, 110, 115, 120, 125, 130, 135, 140, 145, 150, or about 155 repeating disaccharide units. In some embodiments, the dermatan sulfate polymers of the glycosaminoglycan adsorbent comprise from about 22 to about 152 repeating disaccharide units. In some embodiments, the dermatan sulfate polymers of the glycosaminoglycan adsorbent comprise about 22 repeating disaccharide units, about 36 repeating disaccharide units, about 60 repeating disaccharide units, about 65 repeating disaccharide units, about 110 repeating disaccharide units, or about 148 repeating disaccharide units.

In some embodiments, the dermatan sulfate polymers of the adsorbent have a mean molecular weight within the range of from about 10 kDa to about 70 kDa. In some embodiments, the mean molecular weight of the dermatan sulfate polymer is about 10 kDa, or about 12, 14, 15, 20, 25, 30, 35, 40, 45, 50, 55, 60, 65, or about 70 kDa. In some embodiments, the dermatan sulfate polymers of the glycosaminoglycan adsorbent have a mean molecular weight of from about 10 kDa to about 68 kDa. In some embodiments, the dermatan sulfate polymers of the adsorbent have a mean molecular weight of about 10 kDa, about 30 kDa, about 52 kDa, or about 70 kDa.

In some embodiments, the amount of dermatan sulfate included in the adsorbent solid substrate of the glycocalyx-mimetic adsorption media ranges from about 1% to about 25% w/w. In some embodiments, the amount of dermatan sulfate of the adsorbent is about 1%, about 3%, about 5%, about 7%, about 10%, about 12%, about 15%, about 18%, about 20%, about 22%, or about 25% w/w. In some embodiments, the amount of dermatan sulfate of the adsorbent ranges from about 4% to about 22% w/w. In some embodiments, the amount of dermatan sulfate of the adsorbent ranges from about 7% to about 18% w/w.

In some embodiments, the keratan sulfate polymers of the adsorbent comprise from about 10 to about 70 repeating disaccharide units. In some embodiments, the keratan sulfate polymers comprise about 10 repeating disaccharide units, or about 11, 12, 13, 14, 15, 18, 20, 22, 25, 30, 35, 40, 45, 50, 55, 60, 65, or about 70 repeating disaccharide units. In some embodiments, the keratan sulfate polymers of the glycosaminoglycan adsorbent comprise from about 10 to about 68 repeating disaccharide units. In some embodiments, the keratan sulfate polymers of the glycosaminoglycan adsorbent comprise about 11 repeating disaccharide units, about 35 repeating disaccharide units, about 40 repeating disaccharide units, about 56 repeating disaccharide units, or about 67 repeating disaccharide units.

In some embodiments, the keratan sulfate polymers of the adsorbent have a mean molecular weight within the range of from about 5 kDa to about 30 kDa. In some embodiments, the mean molecular weight of the keratan sulfate polymer is about 5 kDa, or about 6, 8, 10, 12, 14, 15, 16, 18, 20, 22, 24, 25, 26, 28, or about 30 kDa. In some embodiments, the keratan sulfate polymers of the glycosaminoglycan adsorbent have a mean molecular weight of from about 5 kDa to about 28 kDa. In some embodiments, the keratan sulfate polymers of the adsorbent have a mean molecular weight of about 5 kDa, about 25 kDa, about 50 kDa, or about 70 kDa.

In some embodiments, the amount of keratan sulfate included in the adsorbent solid substrate of the glycocalyx-mimetic adsorption media ranges from about 0.01% to about 20% w/w. In some embodiments, the amount of keratan sulfate of the adsorbent is about 0.01%, about 0.05%, about 0.1%, about 0.5%, about 1%, about 2%, about 3%, about 5%, about 6%, about 8%, about 10%, about 12%, about 14%, about 15%, about 16% w/w, about 18%, or about 20% w/w. In some embodiments, the amount of keratan sulfate of the adsorbent ranges from about 0.5% to about 15% w/w. In some embodiments, the amount of keratan sulfate of the adsorbent ranges from about 1% to about 5% w/w.

In some embodiments, the hyaluronic acid polymers of the adsorbent comprise from about 10 to about 100,000 repeating disaccharide units. In some embodiments, the hyaluronic acid polymers comprise about 10 repeating disaccharide units, or about 25, 50, 75, 100, 500, 1000, 1500, 2000, 2500, 3000, 3500, 4000, 4500, 5000, 5500, 6000, 6500, 7000, 7500, 8000, 8500, 9000, 10,000, 12,000, 15,000, 20,000, 25,000, 30,000, 35,000, 40,000, 45,000, 50,000, 55,000, 60,000, 65,000, 70,000, 75,000, 80,000, 85,000, 90,000, 95,000, or about 100,000 repeating disaccharide units. In some embodiments, the hyaluronic acid polymers of the glycosaminoglycan adsorbent comprise from about 10 to about 90,000 repeating disaccharide units, or from about 40 to about 80,000 repeating disaccharide units, from about 60 to about 70,000, from about 80 to about 60,000, from about 100 to about 50,000, from about 150 to about 40,000, from about 200 to about 30,000, from about 250 to about 20,000, from about 300 to about 10,000, from about 350 to about 9,000, from about 400 to about 8,000, from about 450 to about 7,000, from about 500 to about 6,000, from about 550 to about 5,000, from about 600 to about 4,000, from about 650 to about 3,000, from about 700 to about 2,000, or from about 750 to about 1,000 repeating disaccharide units. In some embodiments, the hyaluronic acid polymers of the glycosaminoglycan adsorbent comprise about 11 repeating disaccharide units, about 1200 repeating disaccharide units, about 2200 repeating disaccharide units, about 4100 repeating disaccharide units, about 7900 repeating disaccharide units, about 12,300 repeating disaccharide units, about 21,100 repeating disaccharide units, about 55,400 repeating disaccharide units, or about 98,700 repeating disaccharide units.

In some embodiments, the hyaluronic acid polymers of the adsorbent have a mean molecular weight within the range of from about 4 kDa to about 40,000 kDa. In some embodiments, the mean molecular weight of the hyaluronic acid polymer is about 5 kDa, or about 15, 20, 25, 50, 75, 100, 500, 1000, 1500, 2000, 2500, 3000, 3500, 4000, 4500, 5000, 5500, 6000, 6500, 7000, 7500, 8000, 8500, 9000, 10,000, 12,000, 15,000, 20,000, 25,000, 30,000, 35,000, or about 40,000 kDa. In some embodiments, the hyaluronic acid polymers of the glycosaminoglycan adsorbent have a mean molecular weight of from about 5 kDa to about 38,000 kDa, or from about 10 to about 36,000 kDa, from about 12 to about 35,000, from about 18 to about 32,000, from about 28 to about 30,000, from about 35 to about 28,000, from about 42 to about 25,000, from about 46 to about 22,000, from about 52 to about 18,000, from about 64 to about 14,000, from about 78 to about 11,000, from about 120 to about 9500, from about 180 to about 8000, from about 320 to about 5500, from about 460 to about 3500, from about 570 to about 2200, from about 630 to about 1800, or from about 800 to about 1000 kDa. In some embodiments, the hyaluronic acid polymers of the adsorbent have a mean molecular weight of about 4 kDa, about 890 kDa, about 1340 kDa, about 3000 kDa, about 5900 kDa, about 8000 kDa, about 11,900 kDa, or about 34,000 kDa.

In some embodiments, the amount of hyaluronic acid included in the adsorbent solid substrate of the glycocalyx-mimetic adsorption media ranges from about 5% to about 50% w/w. In some embodiments, the amount of hyaluronic acid of the adsorbent is about 5%, about 10%, about 15%, about 20%, about 25%, about 30%, about 35%, about 40%, about 45%, or about 50% w/w. In some embodiments, the amount of hyaluronic acid of the adsorbent ranges from about 8% to about 50% w/w. In some embodiments, the amount of hyaluronic acid of the adsorbent ranges from about 10% to about 50% w/w.

In some embodiments, the adsorbent of the glycocalyx-mimetic adsorption media solid substrate comprises from about 40% to about 96% w/w heparan sulfate, from about 5% to about 30% w/w chondroitin sulfate, from about 1% to about 25% w/w dermatan sulfate, from about 0.01% to about 20% w/w keratan sulfate, and from about 5% to about 50% w/w hyaluronic acid. In some embodiments, the adsorbent comprises from about 50% to about 90% w/w heparan sulfate, from about 10% to about 24% w/w chondroitin sulfate, from about 4% to about 22% w/w dermatan sulfate, from about 0.5% to about 15% w/w keratan sulfate, and from about 8% to about 50% w/w hyaluronic acid.

In certain aspects, the adsorbent of the glycocalyx-mimetic adsorption media solid substrate comprises one or more core proteins selected from the group consisting of syndecan, glypican, perlecan, versican, decorin, biglycan, mimecan, or a combination thereof, in an amount ranging from about 0.001% to about 30% w/w; from about 30% to about 96% w/w heparan sulfate; from about 0.1% to about 30% w/w chondroitin sulfate; from about 0.1% to about 25% w/w dermatan sulfate; from about 0.001% to about 20% w/w keratan sulfate; and from about 0.1% to about 50% w/w hyaluronic acid.

In some embodiments, the solid substrate of the glycocalyx-mimetic adsorption media has the contents of any one of the formulations A-FF in the following Tables 1-8:

TABLE 1

Glycosaminoglycan adsorbent formulations for coating solid substrates

| GAG | Formulation A (% w/w) | Formulation B (% w/w) | Formulation C (% w/w) | Formulation D (% w/w) |
|---|---|---|---|---|
| HS and/or Hep | 30-45 | 40-60 | 50-75 | 55-70 |
| CS | 0.5-12 | 1.0-15 | 2.0-24 | 6.0-24 |
| DS | 0.5-8.0 | 1.0-12 | 1.0-15 | 1.0-10 |
| KS | 0.05-5.0 | 0.5-10 | 1.0-8.0 | 0.5-6.0 |
| HA | 40-50 | 30-40 | 8.0-50 | 20-45 |

TABLE 2

Glycosaminoglycan adsorbent formulations for coating solid substrates

| GAG | Formulation E (% w/w) | Formulation F (% w/w) | Formulation G (% w/w) | Formulation H (% w/w) |
|---|---|---|---|---|
| HS and/or Hep | 96-98 | 80-90 | 90-96 | 50-80 |
| CS | 1.0-2.0 | 3.5-8.0 | 0.5-3.5 | 2.0-12.5 |
| DS | 0.3-0.48 | 1.5-4.0 | 0.5-1.5 | 2.0-22 |
| KS | 0.02-0.2 | 0.8-2.0 | 0.5-1.0 | 0.5-6.0 |
| HA | 0.5-1.5 | 4.2-6.0 | 1.0-4.0 | 15-40 |

TABLE 3

Glycosaminoglycan adsorbent formulations for coating solid substrates

| GAG | Formulation I (% w/w) | Formulation J (% w/w) | Formulation K (% w/w) | Formulation L (% w/w) |
|---|---|---|---|---|
| HS and/or Hep | 70-95 | 60-75 | 45-60 | 30-55 |
| CS | 1.5-25 | 5.0-20 | 3.5-18 | 6.0-40 |
| DS | 1.5-25 | 3.0-18 | 2.0-15 | 1.8-20 |
| KS | 0.5-10 | 1.0-8.0 | 1.5-12 | 0.005-25 |
| HA | 0.5-25 | 1.0-35 | 2.0-45 | 4.0-50 |

TABLE 4

Glycosaminoglycan adsorbent formulations for coating solid substrates

| GAG | Formulation M (% w/w) | Formulation N (% w/w) | Formulation O (% w/w) | Formulation P (% w/w) |
|---|---|---|---|---|
| HS and/or Hep | 30 | 40 | 45 | 50 |
| CS | 7.5 | 17 | 12.25 | 10.5 |
| DS | 10 | 2.975 | 7.75 | 5.5 |
| KS | 2.5 | 0.025 | 5.0 | 4.0 |
| HA | 50 | 40 | 30 | 30 |

TABLE 5

Glycosaminoglycan adsorbent formulations for coating solid substrates

| GAG | Formulation Q (% w/w) | Formulation R (% w/w) | Formulation S (% w/w) | Formulation T (% w/w) |
|---|---|---|---|---|
| HS and/or Hep | 50 | 55 | 60 | 65 |
| CS | 5.5 | 14 | 15 | 9.0 |
| DS | 4.0 | 10 | 11 | 7.0 |
| KS | 0.5 | 3.0 | 1.0 | 3.0 |
| HA | 40 | 18 | 13 | 16 |

TABLE 6

Glycosaminoglycan adsorbent formulations for coating solid substrates

| GAG | Formulation U (% w/w) | Formulation V (% w/w) | Formulation W (% w/w) | Formulation X (% w/w) |
|---|---|---|---|---|
| HS and/or Hep | 70 | 75 | 80 | 85 |
| CS | 12 | 2.5 | 3.8 | 8.5 |
| DS | 6.0 | 2.4 | 0.6 | 3.0 |
| KS | 2.0 | 0.1 | 0.6 | 0.5 |
| HA | 10 | 20 | 15 | 3.0 |

TABLE 7

Glycosaminoglycan adsorbent formulations for coating solid substrates

| GAG or core protein | Formulation Y (% w/w) | Formulation Z (% w/w) | Formulation AA (% w/w) | Formulation BB (% w/w) |
|---|---|---|---|---|
| Core protein* | 0.001-45 | 0.001-35 | 0.001-25 | 0.001-20 |
| HS and/or Hep | 30-45 | 40-60 | 50-75 | 55-70 |
| CS | 0.5-12 | 1.0-15 | 2.0-24 | 6.0-24 |
| DS | 0.5-8.0 | 1.0-12 | 1.0-15 | 1.0-10 |
| KS | 0.05-5.0 | 0.5-10 | 1.0-8.0 | 0.5-6.0 |
| HA | 40-50 | 30-40 | 8.0-50 | 20-45 |

*The core protein can be any one of the following: syndecan, glypican, perlecan, versican, decorin, biglycan, mimecan, or any suitable combination thereof.

TABLE 8

Glycosaminoglycan adsorbent formulations for coating solid substrates

| GAG or core protein | Formulation CC (% w/w) | Formulation DD (% w/w) | Formulation EE (% w/w) | Formulation FF (% w/w) |
|---|---|---|---|---|
| syndecan | 0.05-25 | 0.5-20 | 0.5-18 | 0.5-15 |
| glypican | 0.05-20 | 0.5-18 | 0.5-15 | 0.5-12 |
| perlecan | 0.001-10 | 0.001-7.5 | 0.001-5.0 | 0.001-2.5 |
| versican | 0.001-10 | 0.001-7.5 | 0.001-5.0 | 0.001-2.5 |
| decorin | 0.01-15 | 0.01-10 | 0.01-7.5 | 0.01-5.0 |
| biglycan | 0.01-15 | 0.01-10 | 0.01-7.5 | 0.01-5.0 |
| mimecan | 0.01-15 | 0.01-10 | 0.01-7.5 | 0.01-5.0 |
| HS and/or Hep | 30-45 | 40-60 | 50-75 | 55-70 |
| CS | 0.5-12 | 1.0-15 | 2.0-24 | 6.0-24 |
| DS | 0.5-8.0 | 1.0-12 | 1.0-15 | 1.0-10 |
| KS | 0.05-5.0 | 0.5-10 | 1.0-8.0 | 0.5-6.0 |
| HA | 40-50 | 30-40 | 8.0-50 | 20-45 |

The glycosaminoglycans/core proteins of proteoglycans can be linked onto the surface of the adsorption media by single covalent bond end-point attachment (e.g., covalent attachment through the terminal residue of the HS (and/or Hep), CS, DS, KS, and HA molecules). A single covalent attachment at the terminal group of the molecule to be attached, as compared to non-covalent attachment or multi-point attachment, advantageously provides better control of the orientation of the immobilized molecules while maximizing their surface density. In some embodiments, the end-point attachment of these long chain carbohydrates provides a brush-type molecular surface architecture that leads to a higher concentration of accessible positions on the GAG chains available for sample contacting and/or analyte binding. In some embodiments, full-length GAG chains are used in the glycosaminoglycan adsorbent for coating substrate surfaces. In some embodiments, fragmented GAG chains are used in the glycosaminoglycan adsorbent for coating substrate surfaces.

Covalent attachment of a GAG/core protein to a solid substrate provides control of parameters such as surface density and orientation of the immobilized molecules as compared to non-covalent attachment, providing sample contact and adsorbate binding to the immobilized molecules. In some embodiments, the surface concentration of the adsorbent on the solid substrate is in the range of 0.01 to about 0.5 µg/cm$^2$, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19 or 0.2 g/cm$^2$. In other embodiments, the surface concentration of the absorbent(s) on the solid substrate is in the range of 0.001-2.0 µg/cm$^2$. In another embodiment, the surface concentration of the absorbent(s) on the solid substrate is in the range of 0.005-0.5 µg/cm$^2$.

In some embodiments, the surface concentration of the adsorbent on the solid substrate is in the range of 1 µg/cm$^2$ to 20 µg/cm$^2$, e.g., 1 µg/cm$^2$, 2 µg/cm$^2$, 3 µg/cm$^2$, 4 µg/cm$^2$, 5 µg/cm$^2$, 6 µg/cm$^2$, 7 µg/cm$^2$, 8 µg/cm$^2$, 9 µg/cm$^2$, 10 µg/cm$^2$, 11 µg/cm$^2$, 12 µg/cm$^2$, 13 µg/cm$^2$, 14 µg/cm$^2$, 15 µg/cm$^2$, 16 µg/cm$^2$, 17 µg/cm$^2$, 18 µg/cm$^2$, 19 µg/cm$^2$, and 20 µg/cm$^2$. In other embodiments, the surface concentration of the adsorbent on the solid substrate is in the range of 5 µg/cm$^2$ to 15 µg/cm$^2$, e.g., 5 µg/cm$^2$, 6 µg/cm$^2$, 7 µg/cm$^2$, 8 µg/cm$^2$, 9 µg/cm$^2$, 10 µg/cm$^2$, 11 µg/cm$^2$, 12 µg/cm$^2$, 13 µg/cm$^2$, 14 µg/cm$^2$, and 15 µg/cm$^2$.

In some embodiments, GAGs and/or core proteins are reductively coupled to primary amines on aminated substrates such as aminated beads by reductive amination. Coupling of an open aldehyde form of a reducing end of a GAG chain to a bead results in a stable secondary amine. Non-reducing ends of a GAG chain having a reactive amine can be coupled to a bead with an intermediate having an aldehyde functionality. For instance, the adsorbent is attached to an amine containing substrate by (a) contacting an aminated substrate with an aqueous solution containing a mannose to form a Schiff base intermediate; and (b) contacting the Schiff base with a reducing agent to attach the GAG. GAGs can be dissolved in aqueous solution such as an acidic aqueous solution. The GAG aqueous solution is contacted with an aminated substrate such as an aminated bead. A Schiff's base is generated. The Schiff's base is thereafter reduced with a reducing agent. The reducing agent can be, for example, sodium cyanoborohydride or sodium borohydride. In certain instances, the solid substrate can be an aldehyde-activated bead, which can be reacted with core proteins of proteoglycans having a reactive primary amine.

In some embodiments, covalent attachment of full-length GAG molecules to a surface can be achieved by the reaction of an aldehyde group of the GAG molecule with a primary amino group present on the surface of the adsorption media. An inherent property of all carbohydrates is that they have a hemiacetal in their reducing end. This acetal is in equilibrium with the aldehyde form and can form Schiff's bases with primary amines. These Schiff's bases may then be reduced to stable secondary amines. In some embodiments, full-length GAG molecules are surface immobilized onto the solid substrate by covalent conjugation. In other embodiments, full-length GAGs are covalently attached to said adsorption media via a stable secondary amino group.

In certain instances, various methods of coating solid substrates with adsorbents are disclosed in U.S. Pat. Nos. 8,663,148 and 8,758,286; and U.S. Application Publication Nos. 2009/0136586, 2012/0305482, and US 2014/231357, the disclosures of which are herein incorporated by reference for all purposes.

In some embodiments, the solid substrate of the glycocalyx-mimetic adsorption media can be in the form of a plurality of solid beads or particles. The beads can be made of materials that are sufficiently rigid so as to resist deformation or compaction under the encountered flow rates and pressures. In some embodiments, sufficient substrate rigidity is defined as rigidity producing no significant increase in pressure drop across an adsorption bed during about one hour of flow of water or saline at typical clinical flow rates. For example, a suitable substrate rigidity would produce a less than 10-50% increase in pressure drop relative to the initial pressure drop (e.g., measured within the first minute of flow) when measured at a similar flow rate, e.g., of saline.

The size of the solid substrate can be selected according to the volume of the sample to be treated or other parameters. In some embodiments, each bead of the plurality of rigid polymer beads has an average outer diameter of about 1 μm to about 1 mm, e.g., 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 45 μm, 55 μm, 60 μm, 65 μm, 70 μm, 75 μm, 80 μm, 85 μm, 90 μm, 95 μm, 100 μm, 200 μm, 300 μm, 400 μm, 500 μm, 600 μm, 700 μm, 800 μm, 900 μm, or 1 mm. For example, polyethylene beads from DSM Biomedical (Berkeley, CA) having an average diameter of 300 μm are suitable for the methods and devices disclosed herein. In other embodiments, each bead of the plurality of rigid polymer beads has an average diameter of about 10 μm to about 200 μm, e.g., 10 μm, 15 μm, 20 μm, 25 μm, 30 μm, 35 μm, 45 μm, 55 μm, 60 μm, 65 μm, 70 μm, 75 μm, 80 μm, 85 μm, 90 μm, 95 μm, 100 μm, 105 μm, 110 μm, 115 μm, 120 μm, 125 μm, 130 μm, 135 μm, 140 μm, 145 μm, 150 μm, 155 μm, 160 μm, 165 μm, 170 μm, 175 μm, 180 μm, 185 μm, 190 μm 195 μm, 200 μm or more. Generally, a particle size in the range of 20-200 m such as 10, 20, 30, 40, 50, 60, 70, 80, 90, 100, 110, 120, 130, 140, 150, 160, 170, 180, 190, or 200 m is useful, but in high flow rate applications larger particles may be required. In certain instances, particles at sizes of 120 m and below are preferably used with plasma and serum.

Methods for making such beads are known in the art. For instance, suitable polyethylene beads and other polyolefin beads are produced directly during certain synthesis processes. In some instances, the beads are processed to the required size and shape. Other polymers may need to be ground or spray dried and classified, or otherwise processed to create beads of the desired size distribution and shape.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

The solid substrate may comprise one or more hollow or solid fibers. In an embodiment of the inventive device, wherein the solid substrate comprises hollow fibers, the hollow fibers may preferably comprise a material selected from the group consisting of polysulfones, polyfluorocarbons, polyamides, polynitriles, polypropylenes, cross linked alginates, and cellulose. Other materials commonly used in hollow fibers for medical applications may also be employed. The hollow fiber may preferably comprise a polysulfone.

The size and porosity of the solid substrate should be selected for each application or treatment so as to allow a suitable blood flow rate through the device at an acceptable pressure drop over the device. For certain applications requiring a high blood flow rate and a low pressure drop, a larger diameter particle, pore, hollow fiber or other solid substrate is required. In other applications that do not require a high blood flow rate and a low pressure drop, smaller diameter particles, pores, hollow fibers or other solid substrates may be used. In an embodiment of the present disclosure, wherein the solid substrate is present in the form of hollow fibers, the inner diameter of the fibers may be in the range of 1 m to 1000 m, such as 10, 20, 30, 40, 50, 60, 70, 80, 90, 100, 200, 300, 400, 500, 600, 700, 800, 900 or 1000 m. Generally, an inner diameter in the range of 20-200 m is useful, but in certain applications larger or smaller diameter fibers may be employed.

As described previously, glycocalyx-mimetic adsorption media of the present disclosure are designed to function similarly to a naturally occurring fully-functional glycocalyx barrier. Accordingly, the glycocalyx-mimetic adsorption media acts as an endothelial surface layer to protect and/or maintain glycocalyx function of the damaged glycocalyx barrier. In other words, augmenting impaired glycocalyx barrier function with the glycocalyx-mimetic adsorption media not only enhances and/or restores the impaired glycocalyx barrier function, the glycocalyx-mimetic adsorption media protects and/or maintains the enhance and/or restored glycocalyx barrier function. In addition to augmenting, enhancing, restoring, protecting, and/or maintaining glycocalyx barrier function, the glycocalyx-mimetic adsorption media is capable of binding to the adsorbates which cause glycocalyx barrier dysfunction. As such, a sample obtained from a subject suffering from impaired glycocalyx barrier function will contain adsorbates which bind to the glycocalyx-mimetic adsorption media upon contact, and are thus removed from the sample, thereby forming a treated sample. In some embodiments, the glycocalyx-mimetic adsorption media removes adsorbates from sample, thereby treating the sample, wherein the adsorbates are selected from the group comprising lymphokines, interferons, chemokines, exotoxins, endotoxins, ultra large von Willebrand factor (ULVWF), histones, exosomes, microvesicles, cytokines, tumor necrosis factor (TNF)-alpha, bacterial lipopolysaccharide (LPS), low-density lipoproteins (LDL), and heparin binding protein (HBP).

HBP is an early marker of organ dysfunction. Heparin-binding protein (HBP), released from activated neutrophils, is a potent inducer of vascular leakage. Plasma levels of HBP could be used as an early diagnostic marker for severe sepsis. In other words, high plasma levels of HBP helped identify patients with an imminent risk of developing sepsis with circulatory failure. (See, Linder, A et al., Clin Infect Dis. 2009 Oct. 1; 49(7):1044-50).

In some embodiments, the glycocalyx-mimetic adsorption media reduces the content (e.g., amount, level, etc.) of at least one adsorbate by about 5% to about 100% compared to the adsorbate content (e.g., amount, level, etc.) of the sample prior to treatment. In some embodiments, the glycocalyx-mimetic adsorption media reduces the content of at least one adsorbate by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%>, at least 97%>, at least 98%>, at least 99%>, or greater, compared to the adsorbate content of the sample prior to treatment. In some embodiments, the glycocalyx-mimetic adsorption media reduces the content of at least one adsorbate by about 10% to about 100% compared to the adsorbate content of the sample prior to treatment. The reduction in the levels of an adsorbate can be detected using methods known in the art to detect the transcript (e.g., quantitative polymerase chain reaction) or the adsorbate (protein) directly (e.g., immunoblot, enzyme-linked immunoassay) or indirectly by measuring the activity of the adsorbate (protein) (e.g., degradation of extracellular matrix components).

In some embodiments, the glycocalyx-mimetic adsorption media reduces the content of at least one adsorbate selected from the group comprising lymphokines, interferons, chemokines, exotoxins, endotoxins, ultra large von Willebrand factor (ULVWF), histones, exosomes, microvesicles, cytokines, tumor necrosis factor (TNF)-alpha, bacterial lipopolysaccharide (LPS), low-density lipoproteins (LDL), and heparin binding protein (HBP) by about 10% to about 100% compared to the adsorbate content of the sample prior to treatment. In some embodiments, the glycocalyx-mimetic adsorption media reduces the content of ultra large von Willebrand factor (ULVWF), histones, exosomes, microvesicles, cytokines, tumor necrosis factor (TNF)-alpha, bacterial lipopolysaccharide (LPS), low-density lipoproteins (LDL), heparin binding protein (HBP), or a combination thereof, by about 10% to about 100% compared to the adsorbate content of the sample prior to treatment. In some embodiments, the glycocalyx-mimetic adsorption media reduces the content of tumor necrosis factor (TNF)-alpha, bacterial lipopolysaccharide (LPS), low-density lipoproteins (LDL), heparin binding protein (HBP), or a combination thereof, by about 10% to about 100% compared to the adsorbate content of the sample prior to treatment. In some embodiments, the glycocalyx-mimetic adsorption media reduces the content of tumor necrosis factor (TNF)-alpha by about 10% to about 100% compared to the tumor necrosis factor (TNF)-alpha content of the sample prior to treatment. In some embodiments, the glycocalyx-mimetic adsorption media reduces the content of low-density lipoproteins (LDL) by about 10% to about 100% compared to the low-density lipoproteins (LDL) content of the sample prior to treatment. In some embodiments, the glycocalyx-mimetic adsorption media reduces the content of heparin binding protein (HBP) by about 10% to about 100% compared to the heparin binding protein (HBP) content of the sample prior to treatment.

Also provided herein are methods for treating a condition associated with impaired glycocalyx barrier function in a subject in need thereof, the method comprising: contacting a sample from the subject with a glycocalyx-mimetic adsorption media to (a) enhance and/or restore impaired glycocalyx barrier function and/or (b) remove at least one adsorbate; forming a treated the sample; and infusing the treated sample into the subject, thereby treating the condition associated with impaired glycocalyx barrier function. In some embodiments, the condition associated with impaired glycocalyx barrier function is selected from the group consisting of capillary leak syndrome, edema formation, inflammation, platelet hyperaggregation, hypercoagulation, loss of vascular responsiveness, sepsis, organ failure, atherosclerosis, and diabetes.

One particular example of a condition to be treated according to the methods described herein is sepsis. Sepsis can be defined as a severe endothelial dysfunction syndrome in response to intravascular and extravascular infections causing reversible or irreversible injury to the microcirculation responsible for multiple organ failure. Sepsis is a potentially life-threatening complication of an infection that can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). Sepsis can occur when endothelial and neutrophil cells are activated and chemicals (i.e., inflammatory mediators) are released into the bloodstream to fight infection, triggering inflammatory responses throughout the body. Such chemicals or inflammatory mediators (e.g., lymphokines, interferons, chemokines, exotoxins, endotoxins, ultra large von Willebrand factor (ULVWF), histones, exosomes, microvesicles, cytokines, tumor necrosis factor (TNF)-alpha, bacterial lipopolysaccharide (LPS), low-density lipoproteins (LDL), and heparin binding protein (HBP)) can elicit a cascade of changes in which the body's immune system attacks healthy tissue, damaging multiple organ systems, leading to multiple organ failure in highly perfused organs. Sepsis can progress to septic shock, where blood pressure drops dramatically and can lead to death. Septic shock occurs as a complication of an infection, where toxins can initiate a full-body inflammatory response. Septic shock can occur when the blood pressure drops to a dangerously low level after an infection. Reducing HBP and other inflammatory mediators will modulate the immune response and could act as an organ preservation strategy.

von Willebrand factor (VWF) is a multimeric protein that mediates platelet adhesion and aggregation at sites of vascular injury. Stored in Weibel-Palade bodies within endothelial cells and alpha granules of platelets, VWF is released from stimulated endothelium as hyperactive ultra-large VWF multimers (ULVWF). ULVWF has greater affinity for platelets favoring platelet aggregation, causing platelet activation and microvascular thrombi. The concomitant activation of coagulation factors and blood platelets may result in disseminated intravascular coagulation (DIC) and may also contribute to organ dysfunction. The hyperactive ULVWF relies upon an enzyme known as ADAMTS-13 (a disintegrin and metalloprotease with thrombospondin type-1 motif, member 13) for its cleavage and thus conversion into a less active form. However, deficient proteolysis of ULVWF due to reduced ADAMTS-13 activity results in disseminated platelet-rich thrombi in the microcirculation seen in thrombotic microangiopathy (thrombosis) and organ failure. Decreased levels of ADAMTS-13 are particularly seen in thrombotic thrombocytopenic purpura, liver disease, malignancy, systemic lupus erythematosus, disseminated intravascular coagulation, and severe sepsis. ADAMTS-13 deficiency and elevated plasmas levels of ULVWF are associated with sepsis, resulting in a net accumulation of thrombogenic ULVWF on the surfaces of endothelial cells with disrupted glycocalyx barriers, thus propagating pathological platelet-endothelial interactions, which in combination with other prothrombotic changes seen in sepsis could contribute to enhanced microvascular thrombosis, platelet consumption, disseminated intravascular coagulation, edema, and eventually multi-organ failure. See, e.g., Blockmeyer, C. L., et al. *Haematologica,* 2008, 93, 137-140; Karim, F. et al. *BMC Pediatrics,* 2013, 13(44), 1-5. As such, removing ULVWF and other inflammatory mediators from a patient's blood and/or plasma sample can treat conditions associated with impaired glycocalyx barrier function such as sepsis, capillary leak syndrome, edema formation, inflammation, platelet hyperaggregation, hypercoagulation, loss of vascular responsiveness, organ failure, atherosclerosis, and diabetes.

After treating the sample, the treated sample can be formed through a separation of the sample from the glycocalyx-mimetic adsorption media. As the adsorbate that was present in the untreated sample remains as part of the glycocalyx-mimetic adsorption media, the resulting separated sample is in a cleansed state. The separating can be achieved by, for example, movement of the sample relative to the glycocalyx-mimetic adsorption media. The movement can be by, for example, diffusion or forced convective flow. In some embodiments, the flow of the sample relative to the glycocalyx-mimetic adsorption media is driven by a pump, such as a positive displacement pump, an impulse pump, a velocity pump, a gravity pump, or a valveless pump. In some embodiments, the pump is a centrifugal pump. In some embodiments, the flow of the sample relative to the glycocalyx-mimetic adsorption media is driven by the cardiac activity of the subject.

In therapeutic indications, the cleansed sample is returned by reinfusion into the subject. The cleansed sample can be infused into the subject immediately after it is formed. The cleansed sample can be held for any period of time prior to infusion into the subject. One or more components can be added to the cleansed sample subsequent to its formation and prior to the infusion. In some embodiments, liquid is added to the cleansed sample to adjust its volume subsequent to its formation and prior to the infusion. The infusion can be in the form of a discrete volume of sample cleansed with the method. The infusion can be in the form a continuous or semi-continuous stream. The amount of cleansed sample that can be infused in the claimed methods is not intended to be limited. It can range from less than 1 mL to above 1 L, up to and including the entire blood volume of the patient when the sample comprises blood and when continuous recirculation back to the subject is employed. One or more 'passes' through the adsorption bed may be used if needed. In some embodiments, the cleansed sample is infused into the subject at a rate of about 5 mL/min, about 10 mL/min, about 15 mL/min, about 20 mL/min, about 25 mL/min, about 30 mL/min, about 35 mL/min, about 40 mL/min, about 45 mL/min, about 50 mL/min, about 60 mL/min, about 70 mL/min, about 80 mL/min, about 90 mL/min, about 100 mL/min, about 150 mL/min, about 200 mL/min, about 250 mL/min, about 300 mL/min, about 350 mL/min, about 400 mL/min, about 450 mL/min, about 500 mL/min, about 550 mL/min, about 600 mL/min, about 700 mL/min, about 800 mL/min, about 900 mL/min, or about 1000 mL/min.

In yet another embodiment, the present disclosure provides method for improving oxygen saturation in a subject in need thereof. The method involves contacting a sample from the subject with a glycocalyx-mimetic adsorption media to enhance and/or restore the impaired glycocalyx barrier function, thereby treating the sample; and infusing the treated sample into the subject, wherein the glycocalyx-mimetic adsorption media is a solid substrate having an adsorbent, wherein the adsorbent is a glycosaminoglycan comprising heparin, heparan sulfate, or a mixture thereof.

Normal arterial oxygen is approximately 75 to 100 millimeters of mercury (mm Hg). Values under 60 mm Hg usually indicate the need for supplemental oxygen. Normal pulse oximeter readings usually range from 95 to 100 percent. Values under 90 percent are considered low. The present methods improve low blood oxygen levels to restore them to the normal range. For example, a low range of 80 to 90% on the pulse oximeter is restored to 95-100%. Similarly, values of 50-60 mm Hg are restored to 75-100 mm Hg.

Also provided are devices for augmenting impaired glycocalyx barrier function in a subject in need thereof. The devices are characterized by a cartridge containing the adsorption media, influx and efflux ports to allow the sample to flow into and out of the device, and endplates to prevent substantially all of the adsorption media from exiting the cartridge. One such device is disclosed in U.S. patent application Ser. No. 14/860,589, filed Sep. 21, 2015.

III. EXAMPLES

The following examples are offered to illustrate, but not to limit, the disclosure.

Example 1

This example illustrates the use of a glycocalyx-mimetic adsorption media to remove ultra-large VWF (ULVWF) multimers in a plasma sample from an individual suspected of having sepsis.

A 45-year-old female patient presents to the Emergency Department with evidence of sepsis-like symptoms including chills, dizziness, fatigue, flushing, low body temperature and shivering. The patient's medical history reveals a recent diagnosis of a bladder infection and administration of oral antibiotics including levofloxacin almost 48 hours prior. On examination, she is febrile with a temperature of 101.5° F. and has a low blood pressure (systolic pressure of about 90 mmHg). Physical examination ascertains pain near the patient's kidneys, on the lower sides of the back, and a rash on her legs. A septic screen to diagnose possible bacterial sepsis or systemic inflammatory response syndrome confirms that the female patient does indeed have sepsis as well as ADAMTS-13 values of 26% (which is below the lower limit of normal, 40%) and the presence of ULVWF in the patient's plasma sample is confirmed using gel electrophoresis. See, e.g., Blockmeyer, C. L., et al. *Haematologica,* 2008, 93, 137-140.

The patient is treated for sepsis by first obtaining whole blood from the patient via a catheter and is transfused into a therapeutic cartridge built with glycosaminoglycan adsorbent coated beads of the present disclosure. The therapeutic cartridge comprises a sealed 300 mL adsorption column filled with glycosaminoglycan adsorbent coated beads and is fixed to a vertical stand. The plasma is transfused over the adsorption column multiple times in an iterative fashion. Each time the plasma is passed over the column, ULVWF and other inflammatory mediators in the plasma adhere to the adsorption media and concentration of ULVWF and other inflammatory mediators in the plasma are reduced. The plasma is returned to the patient. The glycosaminoglycan mixture is effective to remove ULVWF from plasma samples and to treat individuals having sepsis.

Example 2

This example shows the removal of Heparin Binding Proteins (HBP) using methods of the present disclosure.

Figure 2B:
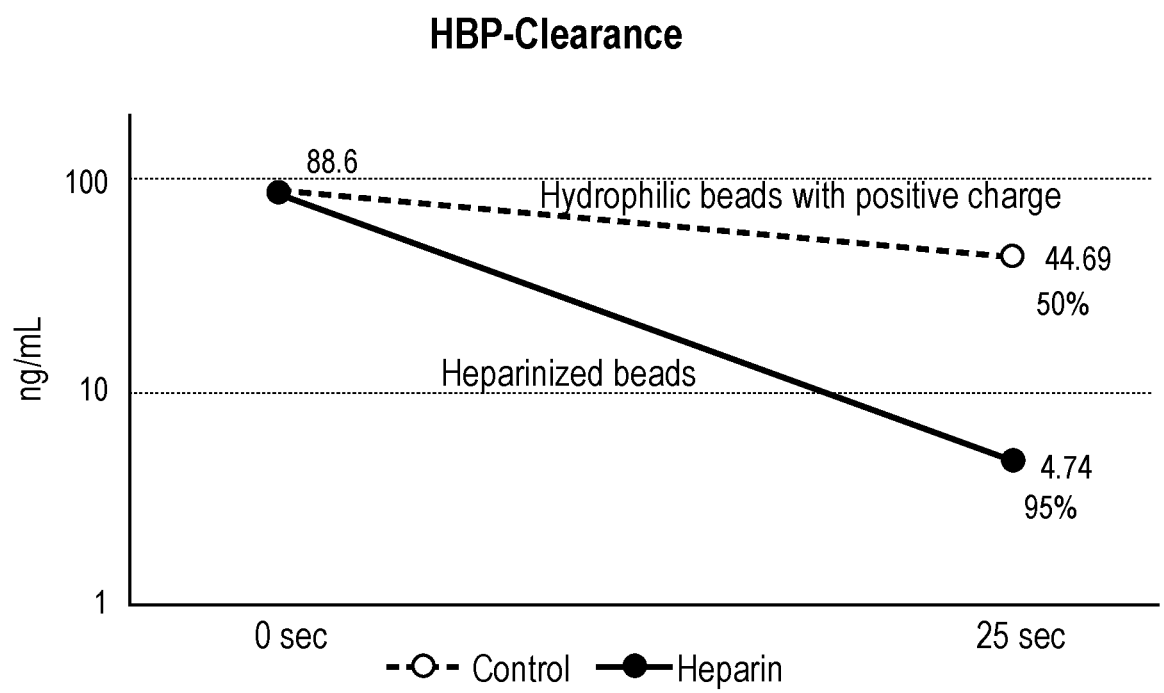
FIG. 2B shows that heparin binding protein (HBP) is adsorbed by heparin.

FIGS. 2A-B show removal of HBP using heparinized beads. FIGS. 2 A-B show that about 99.9% (A) and 95% (B) of the HBP respectively, were removed using heparinized beads. As is shown, the negatively charged control hydrophilic beads (FIG. 2A) removed more HBP than the positively charged hydrophilic beads (FIG. 2B).

Example 3

This Example shows that the methods of the present disclosure improve oxygen saturation in humans having various medical conditions.

The Seraph® 100 Microbind® Affinity Blood Filter device is a sterile single-use, disposable column packed with ultra-high molecular weight polyethylene (UHMWPE) beads, which are surface-modified with non-leaching, end-point-attached heparin and is comprised of the following components and materials:

| Component Description | Materials of Construction |
|---|---|
| Column Body and End Caps | Copolyester, DuraStar ™ Polymer |
| End Plate | Hydrophilic porous polyethylene, pore size 90-130 microns |
| Adsorption media, beads | UHMWPE, particle size 300 microns |
| O-Ring | Medical grade Platinum cured silicone |
| End Point Attached Heparin | Heparin Sodium, USP |
| Adhesive | Two-part epoxy, Loctite |

The Seraph® 100 Microbind® Affinity Blood Filter mechanism of function is as follows: The Seraph® 100 Microbind® Affinity Blood Filter device is an extracorporeal broad-spectrum sorbent hemoperfusion device that is designed to reduce bacteria, viruses, toxins, cytokines and other inflammatory mediators from whole blood. The Seraph® 100 Microbind® Affinity Blood Filter device is designed to share a form factor very similar to other blood filters, such as hemodialyzers or hemoperfusion filters, and therefore is compatible with hemodialysis systems that use industry standard bloodline connectors for ease of operation, training, and utility.

The Seraph® 100 Microbind® Affinity Blood Filter device achieves its intended performance by relying on the natural affinity that many adsorbates (e.g., pathogens, toxins, and inflammatory mediators) have towards surface bound heparin. To achieve an efficient removal of pathogens and other adsorbates, the Seraph® 100 Microbind® Affinity Blood Filter device must present a high surface area of surface bound heparin. This is achieved by filling the device with heparin coated microparticles.

Whole blood is then circulated through the Seraph® 100 Microbind® Affinity Blood Filter device to expose the pathogens and adsorbates to the heparin. The Seraph 100 Microbind Affinity Blood Filter device interacts with the pathogens and various inflammatory mediators via affinity adsorption. Heparin is comprised of many different potential specific binding sites that match chemical sequences of many inflammatory mediators, cytokines, and pathogens. Many microorganisms including bacteria, viruses and parasites attach to heparan sulfate receptors (glycosaminoglycans) on the surface of mammalian cells.

Although the following studies use the Seraph® 100 Microbind® Affinity Blood Filter, each of the formulations in Tables 1-8 (i.e., Formulations A to FF) can be used.

Figure 3:
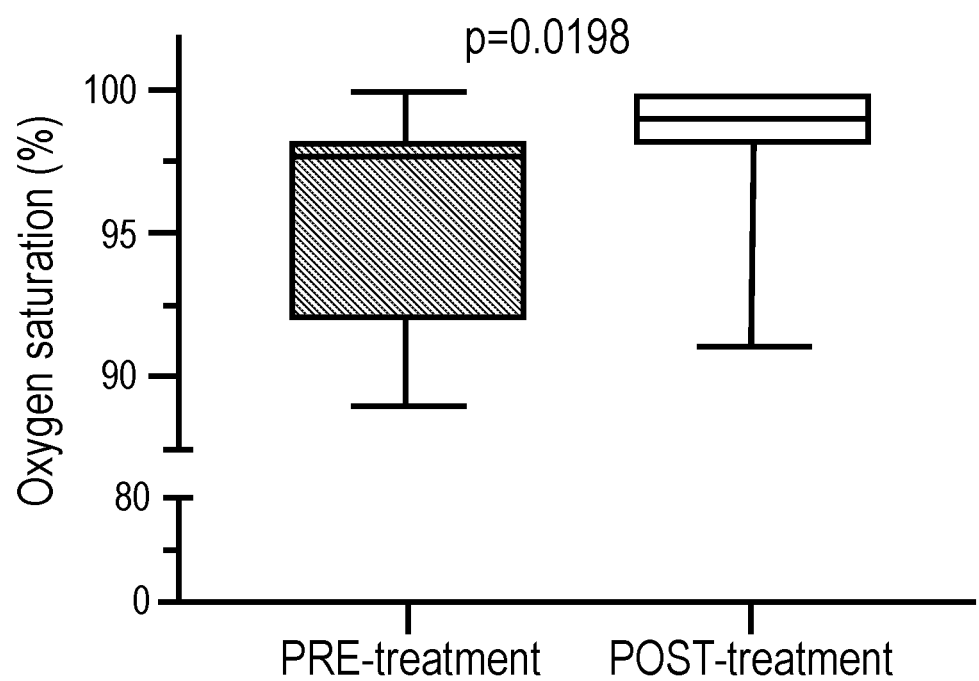
FIG. 3 shows that the methods and devices disclosed herein improve oxygen saturation.

In an exploratory medical device study, 15 subjects underwent a successful procedure using the Seraph® 100 Microbind® Affinity Blood Filter (Seraph® 100). As a patient's blood flows through the Seraph® Microbind® Affinity Blood Filter, it passes microbeads made of polyethylene comprising heparin. No serious adverse events (SAE) were reported while the subjects were connected to the study device. No device complications and no unanticipated serious adverse device effects were reported. No subject died over the course of the trail. The study comprised of 15 dialysis patients with an average age of 72.2 years. During the treatment, a patient received a treatment with Seraph® for approximately 4 hours. It was observed unexpectedly that there was a significant increase in oxygen saturation, as measured by pulse oximetry over the treatment. The data is shown in FIG. 3. The data clearly shows that oxygen saturation in the patient's blood increases to normal values.

Patient Case 1. Persistent Drug Resistant S. aureus

A 70 year old female patient suffering from persistent drug resistant S. aureus for at least 5 days prior to being treated with Seraph® for 5 hours. During the treatment, her bloodstream infection was cleared and her oxygen saturation increased from 96% to 100%.

Patient Case 2. Severe S. aureus Pneumonia

A 86 year old female patient was suffering with severe S. aureus pneumonia with positive blood cultures. She was treated with Seraph® for 6 hours. During the treatment, the device cleared the bloodstream of the bacteria and her oxygen saturation increased from 90% to 96%.

Example 4

This Example shows that the methods of the present disclosure improve hemodynamic stability.

COVID-19 Patient Case 1.

Hemodynamic stability can be explained as stable blood flow. If a person is hemodynamically stable, it means that he/she has a stable heart pump and good circulation of blood. Hemodynamic instability is defined as any instability in blood pressure which can lead to inadequate arterial blood flow to organs. It is also a state where there is a requirement for physiological and mechanical support to ensure there is adequate cardiac input and output or blood pressure.

While most subjects with COVID-19 develop only mild or uncomplicated illness, approximately 14% develop severe disease that requires hospitalization and oxygen support, and 5% require admission to an intensive care unit. In severe cases, COVID-19 can be complicated by the acute respiratory distress syndrome (ARDS), sepsis and septic shock, multiorgan failure, including acute kidney injury and cardiac injury. Older age and co-morbid disease have been reported as risk factors for death, and older age, higher Sequential Organ Failure Assessment (SOFA) score and d-dimer >1 µg/L on admission are associated with higher mortality.

A 67 year old patient was suffering from COVID-19 associated acute respiratory distress syndrome (ARDS) and was in hemodynamic shock. At the time of treatment with Seraph®, his norepinephrine dose was at 0.3 mcg/kg/min to maintain mean arterial pressures above 60 mmHg. During the first three hours of treatment, his norepinephrine dose was decreased to below 0.1 mcg/kg/min and mean arterial pressure (MAPS) were above 80. By the end of his 24 hours of treatment, norepinephrine was discontinued and his MAPs remained stable.

COVID-19 Patient Case 2.

A 59 year old patient was suffering from COVID-19 associated acute respiratory distress syndrome (ARDS) and was entering shock by an increasing requirement of vasopressors and norepinephrine. The patient was treated for 8 hours, in which his norepinephrine dose, was decreased from 0.14 mcg/kg/min with MAPs in the 60 to 0.07 mcg/kg/min with MAPs greater than 80 mmHg. His fraction of inspired oxygen (FiO$_2$) levels also dropped from 70% to 60% indicating his lung function improved.

Discussion

Rapid hemodynamic stabilization is relevant as myocardial injury has been found to be associated with mortality in COVID-19 patients. Because the use of Seraph® for treating COVID-19 patients is still early, the specific mechanism of hemodynamic stabilization is still being investigated. However, mycordial cell damage can be caused by direct interaction with the virus, systemic inflammatory response, destabilized coronary plaque, and aggravated hypoxia. It was shown that elevated Troponin T (TnT) levels correlated with outcome. When TnT was elevated, it was also found that C-reactive protein and NT-proBNT were also elevated. N-terminal pro b-type natriuretic peptide (NT-proBNP) is an inflammatory marker and is produced when the heart is stressed.

NT-proBNT or proBNT levels have been monitored in at least two patients treated with Seraph®. The data is summarized in the chart below. Considering systemic heparin does not interfere with the analysis of NT-proBNP, it is likely that heparin does not bind NT-proBNP. Therefore, the mechanism of NT-proBNP is unknown.

| | Reduction in NT-proBNP or proBNP | | | | |
|---|---|---|---|---|---|
| | NT-proBNP or proBNP (pg/mL) | | | | |
| | Before treatment 1 | After treatment 1 | Before treatment 2 | After treatment 2 | Two days after last treatment |
| COVID-19 Patient 1 (proBNP) | 1541 | 610 | 157 | 97 | NA |
| COVID-19 Patient 3 (NT-proBNP) | 517 | 189 | NA | NA | 48 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for improving oxygen saturation in a subject in need thereof, the method comprising:

a) contacting a sample from the subject with a therapeutically effective amount of a glycocalyx-mimetic adsorption medium to enhance and/or restore the impaired glycocalyx barrier function, thereby treating the sample; and b) infusing the treated sample into the subject, wherein the glycocalyx-mimetic adsorption medium is a solid substrate having an adsorbent, wherein the adsorbent is a glycosaminoglycan comprising heparin, heparan sulfate, or a mixture thereof.

2. The method of claim 1, wherein the adsorbent is a glycosaminoglycan mixture comprising from about 40% to about 96% w/w heparan sulfate and/or heparin, and, optionally, one or more of the following additional adsorbents: from about 5% to about 30% w/w chondroitin sulfate, from about 1% to about 25% w/w dermatan sulfate, from about 0.01% to about 20% w/w keratan sulfate, and/or from about 5% to about 50% w/w hyaluronic acid.

3. The method of claim 1, wherein the glycocalyx-mimetic adsorption medium aids in a member selected from the group consisting of vascular permeability, adhesion of leucocytes, adhesion of platelets, mediation of shear stress, and modulation of an inflammatory process.

4. The method of claim 1, wherein the adsorption medium acts as an endothelial surface layer to protect and/or maintain glycocalyx function.

5. The method of claim 1, wherein the adsorption medium reduces a member selected from the group consisting of capillary leak syndrome, edema formation, inflammation, platelet hyperaggregation, hypercoagulation, and loss of vascular responsiveness.

6. The method of claim 1, wherein the adsorption medium reduces shedding of the glycocalyx during reperfusion of a tissue.

7. The method of claim 6, wherein the tissue is heart tissue during coronary by-pass surgery.

8. The method of claim 6, wherein the tissue is perfused during an organ transplant.

9. The method of claim 1, wherein the method treats acute respiratory distress syndrome (ARDS) in the subject.

10. The method of claim 1, wherein the method improves hemodynamic stability in the subject.

11. The method of claim 1, wherein the adsorption medium reduces shedding of the glycocalyx during sepsis.

12. The method of claim 1, wherein the adsorption medium removes tumor necrosis factor (TNF)-alpha and bacterial lipopolysaccharide (LPS).

13. The method of claim 1, wherein the adsorption medium reduces the risk of organ failure.

14. The method of claim 1, wherein the adsorption medium reduces shedding of the glycocalyx resulting from atherosclerosis or diabetes.

15. The method of claim 1, wherein the adsorption medium removes low-density lipoproteins (LDL).

16. The method of claim 1, wherein the adsorption medium binds heparin binding protein (HBP).

17. The method of claim 1, wherein the adsorption medium binds a member selected from the group consisting of exotoxins, endotoxins, ultra large von Willebrand factor (ULVWF), histones, exosomes, microvesicles and cytokines.

* * * * *